(12) United States Patent
Cabiri et al.

(10) Patent No.: US 10,589,028 B2
(45) Date of Patent: Mar. 17, 2020

(54) PROTECTING A NEEDLE POINT

(71) Applicant: MEDIMOP MEDICAL PROJECTS LTD., Raanana (IL)

(72) Inventors: Oz Cabiri, Macabim-Reut (IL); Ran Hezkiahu, Herzliya (IL)

(73) Assignee: WEST PHARMA. SERVICES IL, LTD., Ra'anana (IL)

( * ) Notice: Subject to any disclaimer, the term of this patent is extended or adjusted under 35 U.S.C. 154(b) by 73 days.

(21) Appl. No.: 15/766,472

(22) PCT Filed: Oct. 10, 2016

(86) PCT No.: PCT/US2016/056223
§ 371 (c)(1),
(2) Date: Apr. 6, 2018

(87) PCT Pub. No.: WO2017/062933
PCT Pub. Date: Apr. 13, 2017

(65) Prior Publication Data
US 2019/0083709 A1    Mar. 21, 2019

Related U.S. Application Data

(63) Continuation of application No. 15/204,542, filed on Jul. 7, 2016, and a continuation of application No.
(Continued)

(51) Int. Cl.
*A61M 5/142* (2006.01)
*A61M 5/158* (2006.01)
(Continued)

(52) U.S. Cl.
CPC .......... *A61M 5/28* (2013.01); *A61M 5/3134* (2013.01); *A61M 5/3202* (2013.01);
(Continued)

(58) Field of Classification Search
CPC .............. A61M 5/3202; A61M 5/3204; A61M 5/3216; A61M 2005/14256;
(Continued)

(56) References Cited

U.S. PATENT DOCUMENTS 1,125,887 A    1/1915  Schimmel
1,321,550 A    11/1919 Platt
(Continued)

FOREIGN PATENT DOCUMENTS

DE    855313 C     11/1952
EP    2364739 A1    9/2011
(Continued)

OTHER PUBLICATIONS

Int'l Preliminary Report on Patentability dated Jan. 18, 2018 in Int'l Application No. PCT/US2016/056223.
(Continued)

*Primary Examiner* — Rebecca E Eisenberg
*Assistant Examiner* — Tasnim Mehjabin Ahmed
(74) *Attorney, Agent, or Firm* — Panitch Schwarze Belisario & Nadel LLP

(57) ABSTRACT

A drug delivery device may include sterile needle covered by removable a sterility preserving protector. The device optionally includes skin contact surface and a needle protector for preventing a stick hazard upon removal of the skin contact surface from an injection site or angle without Removing completely. Optionally, the needle protector may include a shield that interferes with replacement of the needle protector. In some embodiments, the needle cover may interfere with deployment of the needle protector.

24 Claims, 14 Drawing Sheets

Related U.S. Application Data

15/269,248, filed on Sep. 19, 2016, now Pat. No. 10,086,145, which is a continuation-in-part of application No. 14/861,478, filed on Sep. 22, 2015, now Pat. No. 9,987,432.

(60) Provisional application No. 62/281,536, filed on Jan. 21, 2016, provisional application No. 62/284,806, filed on Oct. 9, 2015.

(51) Int. Cl.
    *A61M 5/145* (2006.01)
    *A61M 5/28* (2006.01)
    *A61M 5/32* (2006.01)
    *A61M 5/31* (2006.01)
    *A61M 5/34* (2006.01)

(52) U.S. Cl.
CPC ............ *A61M 5/3204* (2013.01); *A61M 5/34* (2013.01); *A61M 5/1456* (2013.01); *A61M 5/14248* (2013.01); *A61M 2005/1581* (2013.01); *A61M 2005/312* (2013.01); *A61M 2005/341* (2013.01); *A61M 2205/3306* (2013.01); *A61M 2207/00* (2013.01)

(58) Field of Classification Search
CPC ........ A61M 2005/1426; A61M 5/3257; A61M 2005/2073
See application file for complete search history.

(56) References Cited

U.S. PATENT DOCUMENTS

| | | | |
|---|---|---|---|
| 4,710,178 A | 12/1987 | Henri et al. | |
| 4,863,434 A * | 9/1989 | Bayless | A61M 5/3243 604/198 |
| 5,275,582 A | 1/1994 | Wimmer | |
| 5,858,001 A | 1/1999 | Tsals et al. | |
| 6,186,979 B1 | 2/2001 | Dysarz | |
| 6,186,982 B1 | 2/2001 | Gross | |
| 6,189,292 B1 | 2/2001 | Odell et al. | |
| 6,500,150 B1 | 12/2002 | Gross et al. | |
| 6,719,141 B2 | 4/2004 | Heinz et al. | |
| 6,824,529 B2 | 11/2004 | Gross et al. | |
| 6,843,782 B2 | 1/2005 | Gross et al. | |
| 7,967,795 B1 | 6/2011 | Cabiri | |
| 8,496,862 B2 | 7/2013 | Zelkovich et al. | |
| 8,603,028 B2 | 12/2013 | Mudd et al. | |
| 8,721,603 B2 | 5/2014 | Lundquist | |
| 2001/0025168 A1 | 9/2001 | Gross et al. | |
| 2005/0154353 A1 | 7/2005 | Alheidt | |
| 2009/0093792 A1 | 4/2009 | Gross et al. | |
| 2013/0131589 A1 | 5/2013 | Mudd et al. | |
| 2013/0253434 A1 * | 9/2013 | Cabiri | A61M 5/158 604/192 |
| 2014/0163526 A1 | 6/2014 | Cabiri et al. | |
| 2015/0112278 A1 | 4/2015 | Ray et al. | |
| 2015/0157806 A1 | 6/2015 | Knutsson | |

FOREIGN PATENT DOCUMENTS

| | | |
|---|---|---|
| EP | 2452708 A1 | 5/2012 |
| WO | 9721457 A1 | 6/1997 |
| WO | 2005070485 A1 | 8/2005 |
| WO | 2009043000 A1 | 4/2009 |
| WO | 2011101378 A1 | 8/2011 |
| WO | 2011110872 A1 | 9/2011 |
| WO | 2013036602 A1 | 3/2013 |
| WO | 2015048791 A1 | 4/2015 |

OTHER PUBLICATIONS

Inte'l Search Report and Written Opinion dated Nov. 30, 2016 in Int'l Application No. PCT/US2016/056223.

Written Opinion dated Sep. 26, 2017 in Int'l Application No. PCT/US2016/056223.

Communication Pursuant to Rules 161 and 162 dated Apr. 6, 2018 in EP Application No. 16784688.0.

* cited by examiner

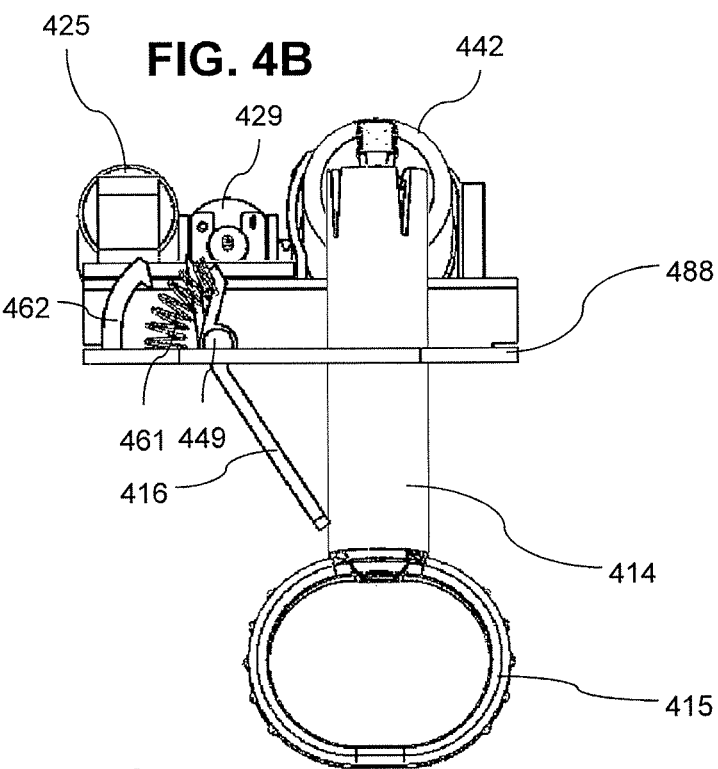
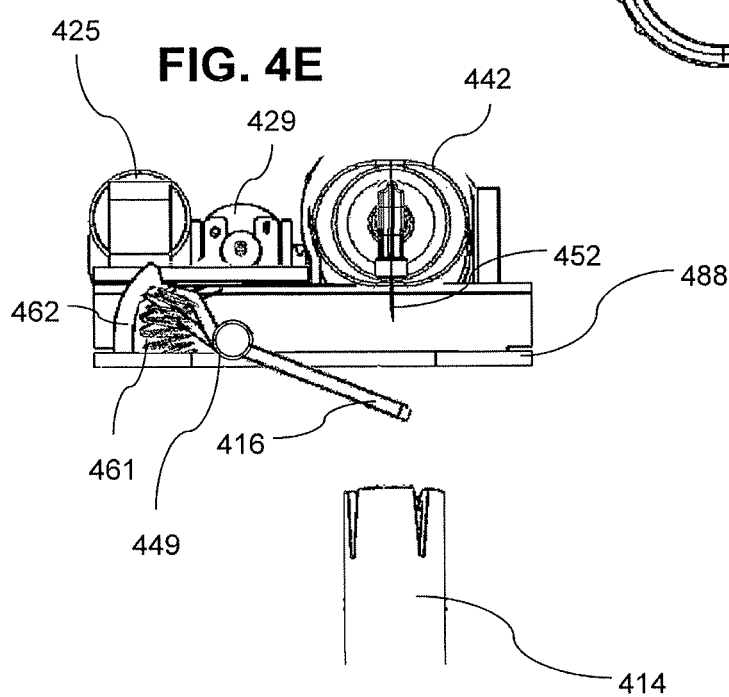

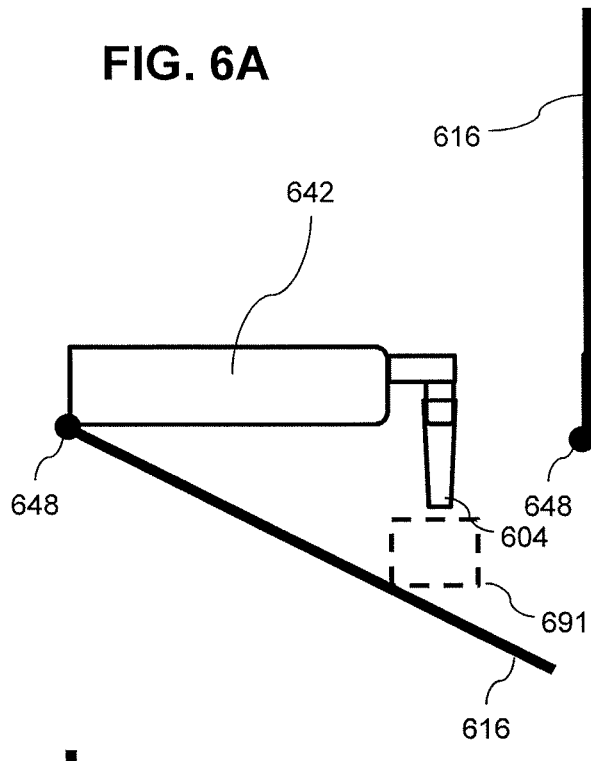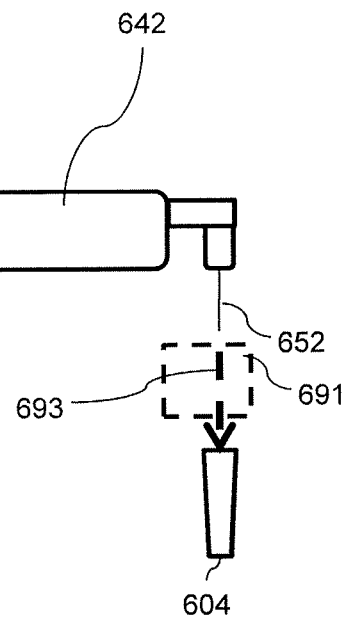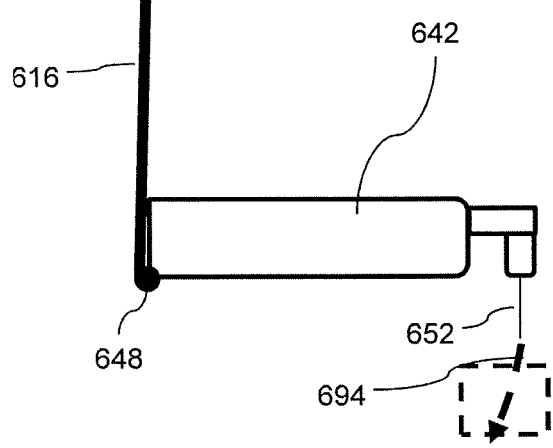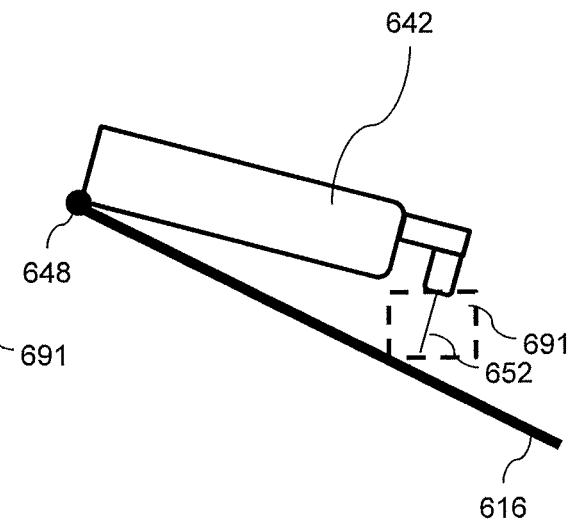

PROTECTING A NEEDLE POINT

This application is a section 371 of International Application No. PCT/US16/56223, filed Oct. 10, 2016, which was published Apr. 13, 2017 under International Publication No. WO 2017/062933 A1, which is a continuation of U.S. application Ser. No. 15/204,542, filed Jul. 7, 2016, which claims the benefit of U.S. Provisional Application No. 62/281,536, filed Jan. 21, 2016 and U.S. Provisional Application No. 62/284,806, filed Oct. 9, 2015; and a continuation of U.S. application Ser. No. 15/269,248, filed Sep. 19, 2016, the disclosures of which are incorporated herein by reference.

FIELD AND BACKGROUND OF THE INVENTION

The present invention, in some embodiments thereof, relates to a protecting a needle point and, more particularly, but not exclusively, to a shield or sensor for needle protection upon removal of a pharmaceutical delivery device from an injection site.

U.S. Pat. No. 6,500,150 discloses, "A drug delivery device having a base member defining a skin-contacting surface, a syringe serving as a reservoir for the drug, and means for expelling drug from the syringe. The syringe is connected to the base member such that the longitudinal axis of the syringe is substantially parallel to the skin surface. A delivery needle is in communication with the syringe. The needle has an angled bend which directs the tip of the needle substantially perpendicular to the skin-contacting surface. In use, the tip of the needle is adapted to penetrate the skin of the subject."

U.S. Pat. No. 6,824,529 discloses "a drug delivery device having a base member defining a skin-contacting surface, a syringe serving as a reservoir for the drug, and means for expelling drug from the syringe. The syringe is connected to the base member such that the longitudinal axis of the syringe is substantially parallel to the skin surface. A delivery needle is in communication with the syringe. The needle has an angled bend which directs the tip of the needle substantially perpendicular to the skin-contacting surface. In use, the tip of the needle is adapted to penetrate the skin of the subject."

U.S. Pat. No. 6,843,782 discloses, "A drug delivery device having a base member defining a skin-contacting surface, a syringe serving as a reservoir for the drug, and means for expelling drug from the syringe. The syringe is connected to the base member such that the longitudinal axis of the syringe is substantially parallel to the skin surface. A delivery needle is in communication with the syringe. The needle has an angled bend which directs the tip of the needle substantially perpendicular to the skin-contacting surface. In use, the tip of the needle is adapted to penetrate the skin of the subject."

U.S. Patent Publication No. 20140163526 discloses that, "an automated injection device may be loaded with a standard type syringe and/or hypodermic needle. Optionally the syringe may be supplied loaded with medicine and/or covered with a sterile needle cover. The syringe may be loaded into the injector with in a sterile state with needle cover in place. Injector may include for example a fastener (for example an adhesive base). In some embodiments, the fastener may assist a user to hold injector steady on the skin of a patient for an extended period. For example, injector may be used to give injections of volume ranging between 0.5 and 3.0 ml over a time period ranging between 30 sec to 180 sec."

U.S. Patent Publication No. 20150088071 discloses, " . . . an activation mechanism (20) and a safety latch (122). The activation mechanism is operative to deploy a needle (116) to protrude out of a housing (112), the needle (116) having a longitudinal axis. The safety latch (122) is movably mounted on the housing (112) and formed with a needle opening (129) to allow the needle (116) to pass therethrough. The safety latch (122) has a first position wherein the needle (116) is aligned to pass through the needle opening (129) and a second position wherein the safety latch (122) is moved with respect to the housing (112) such that the needle (116) is blocked from movement in a direction parallel to the longitudinal axis thereof by a portion of the safety latch (122) distanced from the needle opening (129)."

International Published Patent Application 2015048791 discloses, " . . . a method of preparing a compound device (500) for use. The device may include a sealed component (560) and an active outer surface (579). The outer surface may be protected by a surface cover (589). Preparing the device may include activating the active outer surface by removing the surface cover and exposing an internal portion of the sealed component to the exterior of the device by unsealing the sealed component and synchronizing the activating and said unsealing using a coupler (592) attached to the surface cover and the sealed component."

Additional background art includes U.S. Pat. No. 6,189,292. U.S. Patent Publication No. 20130253434, U.S. Patent Publication No. 2009/093,792, U.S. Pat. No. 7,967,795.

SUMMARY OF THE INVENTION

According to an aspect of some embodiments of the invention, there is provided an injector with a needle stick protector comprising: a frame having a skin contact surface and defining an aperture in the skin contact surface; a needle having a sharp point configured to advance through the aperture; a needle protector removable mounted over the needle; a stick protector movably attached to the frame and biased against the needle protector.

According to some embodiments of the invention, the injector further includes a handle for pulling the needle protector away from the needle thereby freeing the stick protector to moving to a shielding position shielding the sharp point.

According to some embodiments of the invention, the needle protector protrudes through the aperture.

According to some embodiments of the invention, the biasing causes the stick protector to overhang the aperture.

According to some embodiments of the invention, the injector further comprises: a pharmaceutical reservoir in fluid communication with the needle and having a long axis parallel to the skin contact surface.

According to some embodiments of the invention, the needle is rigidly attached to the pharmaceutical reservoir.

According to some embodiments of the invention, a longitudinal axis of the needle at a sharp tip thereof is oriented at an angle of between 30 to 150 degrees with respect to a long axis of the pharmaceutical reservoir.

According to some embodiments of the invention, the pharmaceutical reservoir includes a cylindrical bore and the long axis is the longitudinal axis of the bore.

According to some embodiments of the invention, the needle is sterile and the needle protector protects a sterility of the needle.

According to some embodiments of the invention, the skin contact surface includes an adhesive.

According to an aspect of some embodiments of the invention, there is provided a needle protection system for an autoinjector comprising: a frame including a skin contact surface having an aperture; a sterile needle including a sharp tip on a distal portion thereof, a connection between the needle movably and the frame defining a pathway of movement for advancing the tip through the aperture; a needle protector removably attached to the needle the needle protector removable from the needle along a trajectory defined by sliding of the needle cap along a axis of the distal portion of the needle; a shield connected to the frame for movement between a deployed position blocking the pathway and the trajectory, an open position clearing the pathway and the trajectory and a primed position blocking the trajectory and clearing the pathway.

According to some embodiments of the invention, the needle protector inhibits contamination of the sharp tip.

According to some embodiments of the invention, the needle shield is coupled to the needle protector such that removing the needle protector causes the shield to move from the open position to the shielding position.

According to some embodiments of the invention, the shield blocks replacement of the protector when the shield is in the shielding position.

According to some embodiments of the invention, the system further comprises: a needle driver configured to control the advancing of the needle tip and wherein the shield is interconnected to the needle driver to prevent the advancing when the shield is in the shielding position.

According to some embodiments of the invention, the shield includes a latch that pivotally mounted to the frame.

According to some embodiments of the invention, the shield includes a needle opening large enough to allow the needle tip to pass therethrough but smaller than the aperture, wherein in the primed position the needle is aligned to pass through the needle opening.

According to some embodiments of the invention, in the shielding position the needle is misaligned with the needle opening.

According to some embodiments of the invention, in the primed position the shield is flush with the frame.

According to some embodiments of the invention, the needle protection system further comprises: a pharmaceutical reservoir in fluid communication with the needle and having a long axis parallel to the skin contact surface.

According to some embodiments of the invention, the sterile needle is rigidly attached to the pharmaceutical reservoir.

According to some embodiments of the invention, a longitudinal axis of the needle at the sharp tip is oriented at an angle of between 30 to 150 degrees with respect to a long axis of the pharmaceutical reservoir.

According to some embodiments of the invention, the pharmaceutical reservoir includes a cylindrical bore and the long axis is the longitudinal axis of the bore.

According to some embodiments of the invention, the skin contact surface includes an adhesive.

According to an aspect of some embodiments of the invention, there is provided a needle protection system for an autoinjector comprising: a frame including a skin contact surface having an aperture; a needle including a sharp tip, a movably connected to the frame for advancing the tip through the aperture; a lock interconnected to the needle for controlling the advancing; a needle protector removably attached to the needle; the needle protector removable from the needle along a trajectory defined by sliding of the needle cap along a axis of the needle; stick protector interconnected with the lock and connected to the frame for movement between two positions: a closed position wherein the stick protector blocks the trajectory for removal of the needle protector; an open position wherein the stick protector secures the lock to prevent the advancing.

According to some embodiments of the invention, the needle protector protrudes through the aperture.

According to some embodiments of the invention, the needle protection system further comprises: a pharmaceutical reservoir in fluid communication with the needle and having a long axis parallel to the skin contact surface.

According to some embodiments of the invention, the needle is rigidly attached to the pharmaceutical reservoir.

According to some embodiments of the invention, a longitudinal axis of the needle at the sharp tip is oriented at an angle of between 30 to 150 degrees with respect to a long axis of the pharmaceutical reservoir.

According to some embodiments of the invention, the pharmaceutical reservoir includes a cylindrical bore and the long axis is the longitudinal axis of the bore.

According to some embodiments of the invention, the needle is sterile and the needle protector protects a sterility of the needle.

According to some embodiments of the invention, the skin contact surface includes an adhesive.

According to an aspect of some embodiments of the invention, there is provided a system for protecting a needle of a wearable pharmaceutical delivery device comprising: an outer surface the pharmaceutical delivery device including a skin contact surface, the skin contact surface including at least a open portion defining an opening; a pharmaceutical reservoir in fluid communication with the needle and having a long axis parallel to at least one surface selected from the open portion of the skin contact surface and another portion of the skin contact surface; a needle driver connected to the needle and movable mounted to the open portion of the skin contact surface for advancing a tip of the needle through the opening and outward from the skin contact surface; a switch interconnected between the needle driver and the open portion of the skin contact surface; the switch enabling the advancing in response to an inward pressure on the outer surface of the device.

According to some embodiments of the invention, during delivery of the pharmaceutical the open portion is flush to the another portion.

According to some embodiments of the invention, the needle is sterile and further comprising: a needle cap protecting a sterility of the needle and blocking the switch and wherein removing the needle cap from the needle enables the switch.

According to some embodiments of the invention, the switch is biased outward from the outer surface of the pharmaceutical device.

According to some embodiments of the invention, the needle is rigidly attached to the pharmaceutical reservoir.

According to some embodiments of the invention, a longitudinal axis of the needle at the tip is oriented at an angle of between 30 to 150 degrees with respect to the long axis of the pharmaceutical reservoir.

According to some embodiments of the invention, the pharmaceutical reservoir includes a cylindrical bore and the long axis is the longitudinal axis of the bore.

According to some embodiments of the invention, the skin contact surface includes an adhesive.

According to an aspect of some embodiments of the invention, there is provided a system a wearable pharmaceutical delivery device comprising: an outer surface the pharmaceutical delivery device including a skin contact surface, the skin contact surface defining an opening; a pharmaceutical reservoir in fluid communication with a needle and having a long axis parallel to the skin contact surface; a needle cap protecting surrounding a tip of the needle of to protect the tip from contamination; a needle driver connected to the needle and movable mounted to the skin contact surface for advancing a tip of the needle through the opening and outward from the skin contact surface; and wherein removing the needle cap from the needle opens a pathway of movement the reservoir for the advancing.

According to some embodiments of the invention, the needle is sterile and the needle cap protecting a sterility of the needle.

According to some embodiments of the invention, the needle is rigidly attached to the pharmaceutical reservoir.

According to some embodiments of the invention, a longitudinal axis of the needle at the tip is oriented at an angle of between 30 to 150 degrees with respect to the long axis of the pharmaceutical reservoir.

According to some embodiments of the invention, the pharmaceutical reservoir includes a cylindrical bore and the long axis is the longitudinal axis of the bore.

According to some embodiments of the invention, the skin contact surface includes an adhesive.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 4A-4E are perspective views of drug delivery device with a needle shield latch in accordance with an embodiment of the current invention;

FIGS. 6A-6D are schematic illustrations of an injector having a non-linear movement and a shield in accordance with an embodiment of the present injections;

DESCRIPTION OF SPECIFIC EMBODIMENTS OF THE INVENTION

Overview

Figure 1:
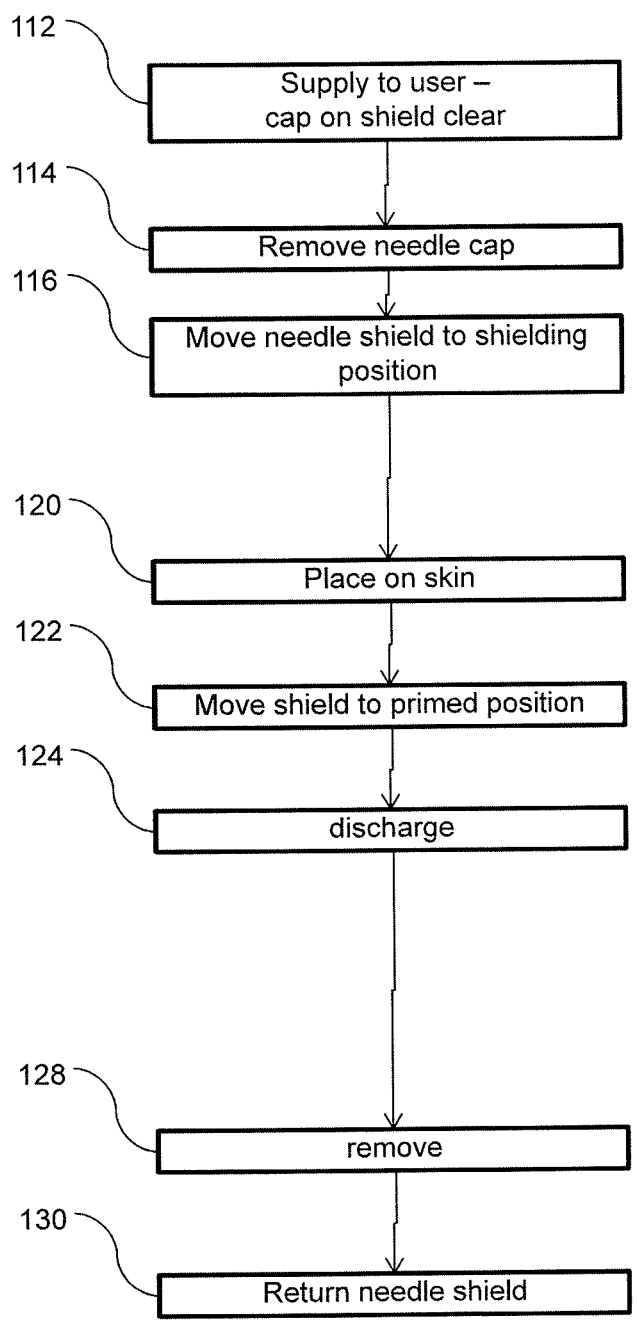
FIG. 1 is a flow chart illustration of a method of shielding a needle in accordance with an embodiment of the present invention.

The present invention, in some embodiments thereof, relates to a protecting a needle point and, more particularly, but not exclusively, to a shield or sensor for needle protection upon removal of a pharmaceutical delivery device from an injection site.

An aspect of some embodiments of the current invention relates to a needle cap which interferes with deployment of a needle protector of a drug discharge device (sometimes a needle cap is referred to as a rigid needle shield RNS). Optionally, the needle protector may be deployed when the cap is removed. In some embodiments, deploying the needle protector may activate the injector.

An aspect of some embodiments of the current invention relates to a pharmaceutical delivery device (for example a drug delivery device, for example an injector) including needle protector that interferes with removal of a needle cap. For example, when the shield and/or sensor is deployed it may block a trajectory of movement of the cap. Optionally the shield and/or sensor has a non activated position which clears the cap. For example, after the cap is removed from the needle, the shield and/or sensor may move from the non active position to a deployed position.

An aspect of some embodiments of the current invention relates to a needle shield and/or sensor that in a deployed state interfere with replacing a needle cap of the injector. Optionally, when the injector is activated and/or primed the sensor and/or shield is deployed.

An aspect of some embodiments of the current invention relates to a needle shield for a drug injector that moves between three states. For example the needle shield may have an open position (for example a pulled back position). The pulled back position may allow a needle cap and/or a cap removal tool to protrude into and/or out of the injector. Optionally, when the needle cap is removed, the needle shield may move to a shielding position. In the shielding position the shield may block exposure of the needle tip. Alternatively and/or additionally the needle shield may have a primed position. In the primed position an opening in the shield may be aligned with a needle, allowing the needle to protrude from the injector. Optionally before the needle of the injector is deployed, the shield may move from the shielding position to the primed position. For example, the shield may move from the shielding position to the primed position when the injector is placed on the skin of a subject. Optionally when the shield is in the shielding position the needle may be prevented from deploying. Optionally, the needle shield may move from primed position to the shielding position when the injector is removed from the skin of a subject. For example while the needle is deployed the needle shield may move from the primed position to a deployed position (for example the shielding position) by a slight bending (elastic and/or inelastic) of the needle. Once the needle shield is in the shielding position with the needle deployed the shield is optionally prevented from returning to the primed position, for example by being blocked by the needle and/or locked. Alternatively or additionally the needle may retract at the end of injection.

In some embodiments, a needle cap may protect a needle before use of the device. Optionally, the needle protector may prevent a stick hazard after removal of the needle cap. For example, the needle protector may prevent a stick hazard upon removal of the device from an injection site.

In some embodiments a needle protector may include a shield that shields a needle point to prevent a stick hazard. Optionally the shield will extend past the needle tip to prevent the stick hazard. Alternatively or additionally, a needle protector may include a skin sensor that senses when a skin contact surface of an injector is in contact with and next to an injection site. In some embodiments, a shield may also include a skin sensor and/or the skin sensor may also shield the needle tip.

In some embodiments a sensor and/or needle shield may include a skin contact surface. Alternatively or additionally the sensor and/or shield may extend away from a skin contact surface. Optionally, the skin contact surface may include an adhesive for adhering to a skin of a user. For example, the skin contact surface maybe adhered to the skin in the vicinity of a needle insertion location. In some embodiments, a shield and/or sensor may move between positions in response to an interaction with a skin of a user. For example, when a shield is pushed against a skin of a user the shield may move from a shielding position to a primed position. Alternatively or additionally, when an injector is taken away from the skin of a user a shield and/or a sensor may move to a shielding position and/or a deployed position. For example, when a skin contact surface moves away from the skin, the injector may be switched from an active state to a protected state. Alternatively or additionally, when a housing of an injector moves away from a skin contact surface the injector may be switched from an active state to a protected state. Movement of the sensor and/or shield may cause the injector to switch states. In some embodiments, an injector will include a needle with a sharp tip. For example the sharp tip may be connected to a straight portion of the needle. Optionally the needle cap covers and/or surrounds the straight portion of the needle. For example, the needle cap may have an elongated form and/or be mounted coaxial to the straight portion of the needle. Optionally, a proximal end of the straight portion is connected to a reservoir and/or a neck thereof and/or a needle holder. For example, the proximal end of the needle cap may attach and/or seal to the reservoir and/or the neck thereof and/or to the needle holder. In some embodiments, the needle cap may protect the needle and/or a tip thereof from physical damage, from harming others (e.g. a sharp stick hazard) and/or from contamination (for example the cover may preserve sterility of the needle and/or needle tip).

In some embodiments, the needle cap may be removed from the needle by longitudinal movement. Optionally, the needle cap may be pulled away from the needle with a force of no more than 0.5 Kg. Alternatively, the needle cap may be pulled away from the needle with a force ranging between 0.5 Kg to 1.0 Kg force and/or with a force ranging between 1.0 Kg to 2 Kg force and/or no more than with a force ranging between 2.0 Kg to 3 Kg force and/or with a force ranging between 3.0 Kg to 6 Kg force.

In some embodiments, a needle may be extended, and/or inserted into an injection zone along a linear path. Alternatively or additionally a needle may be extended and/or inserted along a curved path. For example, the needle may be extended and/or inserted by rotating around a pivot. Optionally, while pivoting, the needle may move in a longitudinal direction (the change in direction of movement may coincide with changes in direction of the axis of the needle).

In some embodiments, a needle shield and/or a sensor may be biased to a shielding and/or deployed configuration. Optionally, when a needle cap is covering a needle, the cap interferes with the shield and/or sensor, inhibiting movement to the biased position. Optionally, in some positions a deployed needle interferes with movement of the sensor and/or shield. Optionally, removal of a needle cap may activate an injector. Optionally, removal of a needle cap may cause peeling of an adhesive liner from an adhesive. For example, the adhesive liner may be connected to the needle cap and/or a needle cap puller. For example, the adhesive may be connected to a skin contact surface.

In some embodiments a needle shield may include an aperture through which a needle cap is removed. For example the width of the aperture may range between 1 mm to 3 mm and/or between 3 mm to 8 mm and/or between 8 mm to 15 mm. Optionally, the aperture may be round. Alternatively or additionally it may have a different shape. In some embodiments a shield may not have an aperture for a cap. For example, the shield may open and/or clear an aperture in the housing of the device. Optionally, the cap may be removed through the aperture in the housing. Optionally the aperture in the housing may fit the shield. For example the aperture in the housing may have a width and/or length between 1 to 5 mm and/or between 5 to 10 mm and/or between 10 to 20 mm and/or between 20 to 40 mm and/or between 40 to 80 mm and/or between 80 to 160 mm. Optionally the aperture in the housing may be rectangular and/or have a different shape.

In some embodiments a shield and/or a housing may include a needle opening. For example, a needle opening may be smaller than an aperture for a cap. For example, the width of a needle opening may range between 0 to 0.5 mm and/or between 0.5 to 1 mm and/or between 1 to 2 mm and/or between 2 to 4 mm. Alternatively or additionally, a needle may pass through the aperture through which passes the needle cap.

In some embodiments, a drug delivery device (for example an injector) may include a prefilled sterile cartridge including a cylindrical barrel directly connected to a hypodermic needle covered by a sterile needle cap. In some embodiments, the user removes the sterile needle cap from the prefilled sterile syringe before use. Optionally removing the needle cap activates the device and/or peels an adhesive cover and/or triggers deployment of a needle shield from an open position to a shielding position. In some embodiments, placing a base of the device on the skin of a subject moves the needle shield into a primed position.

In some embodiments, the device discharges a drug into the subject with the axis of the prefilled syringe substantially parallel to the base of the device and/or the skin of the subject. Optionally a needle mounted on the cartridge may be inserted into the skin of the subject and/or may serve as a fluid path directly from the cartridge to the subject. Optionally, removing the device from the skin of the subject redeploys the needle shield and/or deactivates the device.

In some embodiments the drug delivery device may include a prefilled syringe and/or reservoir with a needle and/or hub at an angle to the axis of the barrel of the reservoir. For example, the drug delivery device may include a needle shield and/or a needle retraction mechanism. For example, the delivery device may include an asymmetric syringe and/or plunger seal. For example, the delivery device may include a needle cap and/or cover remover.

In some embodiments, a single use drug delivery device (for example an injector for example an auto-injector, a patch injector, and/or a bolus injector; for example an injector may be hand held and/or worn on the body) may come preloaded with a drug. For example the device may include cartridge. Optionally the cartridge includes a syringe with a sterile hub and/or sterile needle mounted at an angle to the axis of the syringe barrel. The syringe is optionally prefilled with a drug. Optionally the device may include a needle shield and/or a status indicator. Optionally the device may include an attachment mechanism, for example an adhesive for attaching to a subject.

In some embodiments a cartridge may be installed to the delivery device before assembly and/or before being shipped to a retailer and/or a health provider and/or a user. Alternatively or additionally the cartridge may be installed into the drug delivery device by a user, for example a health provider (for example a nurse and/or a pharmacist and/or a doctor and/or a health aid) and/or a subject of the injection (e.g. a patient receiving the drug) and/or a caretaker.

In some embodiments the device may have bilateral symmetry. For example, the user interface of the device may have bilateral symmetry.

DETAILED EMBODIMENTS

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Method of Delivering a Drug

FIG. 1 is a flow chart illustration of a method of delivering a drug and/or shielding a needle in accordance with an embodiment of the current invention. In some embodiments, an injector may include a needle cover that interferes with a needle shield.

In some embodiments, an assembled injector (with the cartridge installed) may be supplied 112 to a user. Optionally as supplied 112 to the user, the cartridge and/or hub and/or the needle may be sterile and/or covered with a sterile needle cap. Optionally, the injector may have a needle shield. For example, while the needle cap is in place the needle shield may be in an open position, allowing the access to the needle cap. For example, when the needle shield is in the open position there may be space for the cap and/or a cap remover to protrude out of the injector. For example, in the open position, the needle shield may retract. In some embodiments the needle shield may pivot and/or slide from one position and/or state to another. Alternatively or additionally the cartridge and/or the injector may be supplied 112 to the user separately and/or may be assembled by the user.

In some embodiments, before use of an injector, the needle cap may be removed 114. For example, the needle cap may be pulled off of the cartridge through an aperture in the injector housing. Optionally removing 114 the needle cap may cause the delivery device to be activated 116 and/or the needle shield to move to a shielding position. For example, the cap and/or a removal tool may be connected to a switch and/or a battery insulator and/or an adhesive protector. Removing the cap optionally activates the switch and/or causes removal of the battery insulator and/or removal of the adhesive protector. Once activated 116, the delivery device optionally indicates that it is ready to be placed on a subject. Optionally, once the needle shield is in the shielding position it may prevent replacement of the needle cap. Optionally, when the needle shield is in the shielding position it may prevent exposure of the needle. For example, in the shielding position, the needle shield may block the needle tip from extending out of the injector. Alternatively or additionally, when the shield is in the shielding position the needle extension mechanism may be locked and/or disabled thereby preventing extension of the needle out of the injector and/or in the shielding position the needle shield may shield an extended needle tip.

In some embodiments, the injector is placed 120 on the skin of a subject. For example, the delivery device may be placed 120 on the skin of the subject after activation 116. Optionally placement on the skin causes the needle shield to move 122 to a primed position. For example, the shield may be pushed by the skin of the subject into the primed position. Movement 122 of the shield into the primed position may cause extension of a needle from the injection device and/or insertion of the needle through the skin of the subject. For example, the shield may collapse inward exposing the needle and/or allowing the needle to enter the subject and/or movement 122 of the shield may trigger an insertion mechanism. Alternatively or additionally, movement 122 of the shield into the primed position may open a path for the needle to exit the injector. For example, movement 122 of the shield into the primed position may align an opening in the shield to the needle allowing the needle to be extended out of the device, for example through the opening in the needle cap. Alternatively or additionally, an additional step may cause insertion of the needle, for example pushing a button and/or pushing a portion of the injector towards the skin of the subject.

After insertion of the needle, a drug may be delivered 124 into the subject. For example the needle may be hollow and the drug may be delivered 124 through the needle into the subject. Optionally, once injection has completed the device may indicate that injection is finished and/or that the device may be removed. Optionally when a malfunction occurs (for example an occlusion of the fluid path) an indicator may indicate that a malfunction has occurred and/or that the injector should be removed. In some embodiment, the needle may retract upon completion of injection and/or upon certain malfunctions. Alternatively or additionally, the needle may remain extended after delivery 124.

In some embodiments, after delivery 124 and/or error and/or when indicated to do so, a user may remove 128 the injector from the skin of the subject. In some embodiments when the injector is removed 128, the needle shield may redeploy 130. Redeployment 130 of the needle protector may protect the needle and/or shut down the device. Alternatively or additionally, needle retraction may protect the needle. Alternatively or additionally, the device may shut down and/or be disabled immediately after completion of delivery 124 and/or upon certain malfunctions. Alternatively or additionally, the device may shut down and/or be disabled after a certain time period after the completion of delivery 124 and/or upon certain malfunctions.

Figure 2:
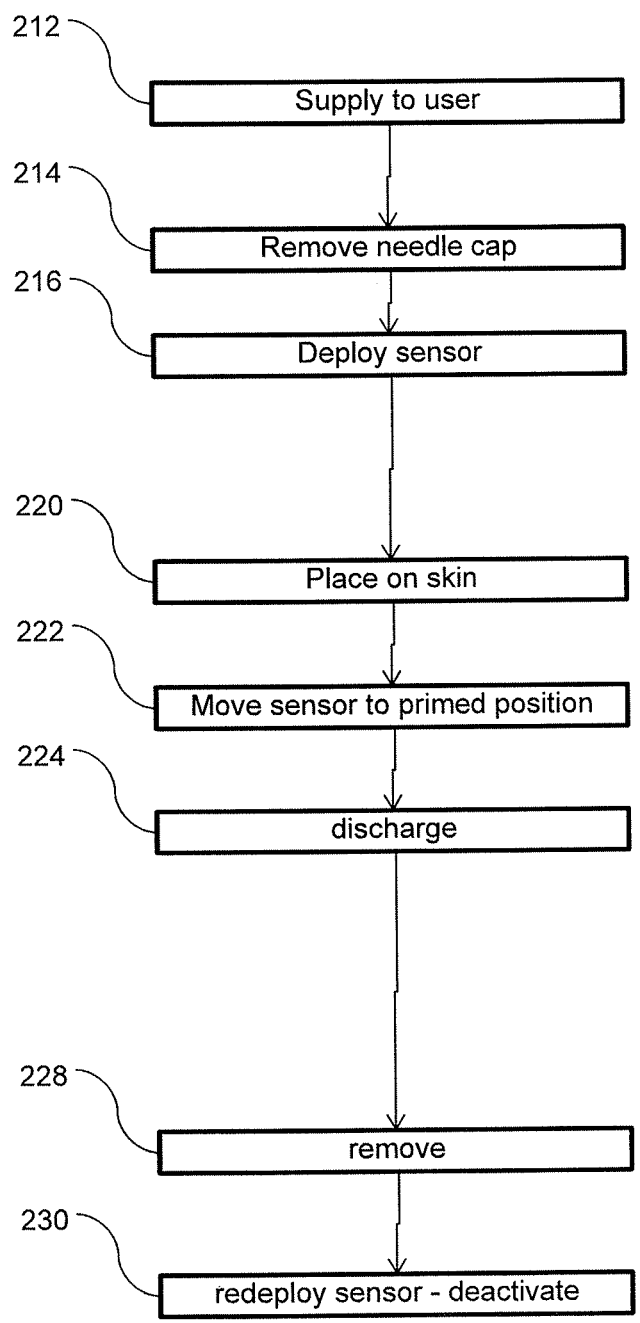
FIG. 2 is a flow chart illustration of a method of protecting a needle in accordance with an embodiment of the present invention.

FIG. 2 is a flow chart illustration of a method of protecting a needle in accordance with an embodiment of the present invention. In some embodiments an injector is supplied 212 to a user with a sterile needle protected by a needle cap. Optionally, removing 214 the needle cap may facilitate activation, priming 222 and/or use of the device.

In some embodiments the needle cap may protect a needle from contamination and/or may inhibit priming 222, activation and/or use of the device. For example, while the needle cap is in place protecting the needle, the needle cap may interfere with deployment 216 of a skin sensor. Optionally, until the skin sensor is deployed 216 a needle driver may be disabled. Alternatively or additionally, the needle cap, while in place over the needle, may interfere with a moving 222 a sensor to a primed position. For example, the sensor may be triggered by pushing an appendage toward a housing and/or base of the device. For example, when the device is placed 220 against the skin of a user a sensor and/or shield may be pushed toward the base and/or housing. For example, the needle cap may interfere with movement of the appendage toward the base. In some embodiments, the needle cap may be interconnected to an adhesive liner and/or a battery insulator. Optionally removal of the needle cap may cause peeling of the adhesive liner away from an adhesive and/or removal of the battery insulator. Optionally removal of the needle cap may facilitate adhering the device (for example a base thereof and/or the skin sensor) to an injection site. Alternatively or additionally, removal of the needle cap may activate the device.

In some embodiments, once the needle cap has been removed 214, returning the cap may be inhibited. For example, removing 214 the cap may release a sensor to partially and/or completely block a needle aperture. In some embodiments, partial blockage of the aperture may inhibit returning the cap onto the needle.

In some embodiments, moving 222 the sensor to a primed position may facilitate use of the device. For example, moving 222 the sensor to a primed position may unlock a needle insertion switch and/or trigger needle insertion and/or trigger discharge 224 of a drug.

In some embodiments, removing 228 the injector from the skin of a user releases and/or redeploys 230 a skin sensor. Optionally, releasing and/or redeploying 230 of the skin sensor deactivates 230 the device and/or locks the device in a neutralized state (for example with a needle protected and/or with drug discharge disabled).

Injector Apparatus

Figure 3:
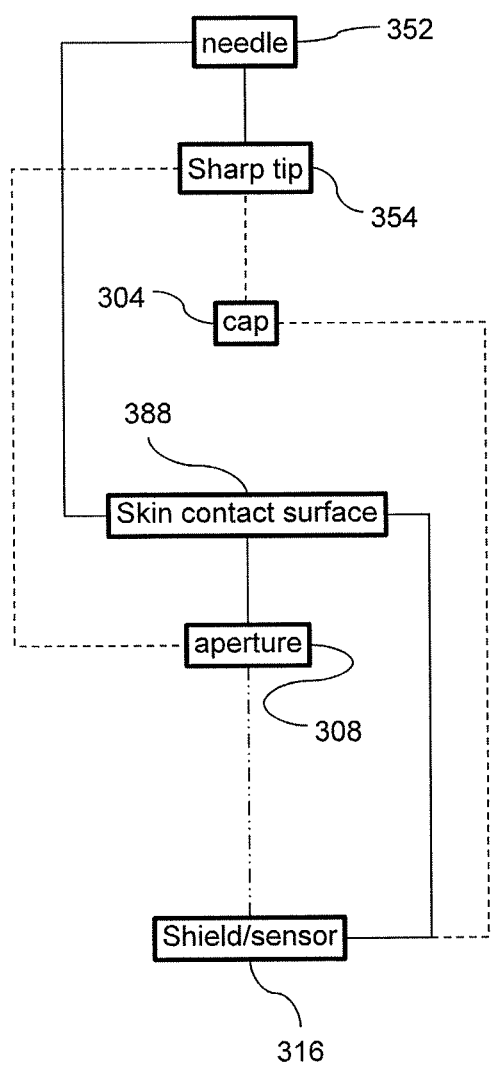
FIG. 3 is a block diagram illustrating a system for protecting a needle in accordance with an embodiment of the present invention.

FIG. 3 is a block diagram illustrating an apparatus for protecting a needle in accordance with an embodiment of the present invention. In some embodiments, a needle cap interacts with a needle shield and/or a sensor.

In some embodiments, an injector includes a skin contact surface 388 which is movably connected (for example, via a frame that may be part of for example a housing) to a needle 352 and/or a shield and/or sensor 316.

In some embodiments, the needle includes a sharp tip that which may move through an optionally aperture 308 in the skin contact surface. Alternatively or additionally, the needle tip may move with respect to surface 388 across and edge thereof.

In some embodiments, all or part of needle 352 (for example sharp tip 354) may be surrounded and/or protected by a needle cap 304. For example, needle cap may protect tip 354 from physical damage and/or may protect tip 354 from contamination (for example preserving sterility of tip 354). Alternatively or additionally, cap 304 may inhibit a sharp stick event (a stick hazard) by covering sharp tip 354.

In some embodiments, shield and/or sensor 316 may shield tip 354 to inhibit a stick hazard. Alternatively or additionally, shield and/or sensor 316 may trigger and/or inhibit actions of the injector. For example, in some states, a shield/sensor 316 may inhibit activation of the device. Optionally in some states shield/sensor may facilitate activation and/or use of the device. For example, when shield/sensor 316 is in an open and/or a deployed state, the device may not function and/or needle 352 may be locked (for example in a retracted state). Optionally when shield/sensor 316 is in a primed state the injector may function and/or needle 352 may be released. In some states shield/sensor 316 may totally and/or partially block aperture 308.

In some embodiments, shield/sensor 316 may be included in skin contact surface 388. For example, in a primed state, an outer surface of shield/sensor 316 may be flush to skin contact surface 388. Optionally, aperture 308 may pass through shield/sensor 316.

In some embodiments, cap 304 may interact with shield/sensor 316. For example, while cap 304 is in place on needle 352, shield/sensor 316 may blocked and/or interfere with moving shield/sensor 316 from an open position to a primed and/or deployed position. Optionally or additionally, when sensor/shield 316 is in the shielding and/or primed position movement of cap 304 may be inhibited. For example sensor/shield 304 may prevent removal of cap 304 and/or reinsertion of cap 304 after it has been removed.

Needle Shield Latch

Figure 4A:
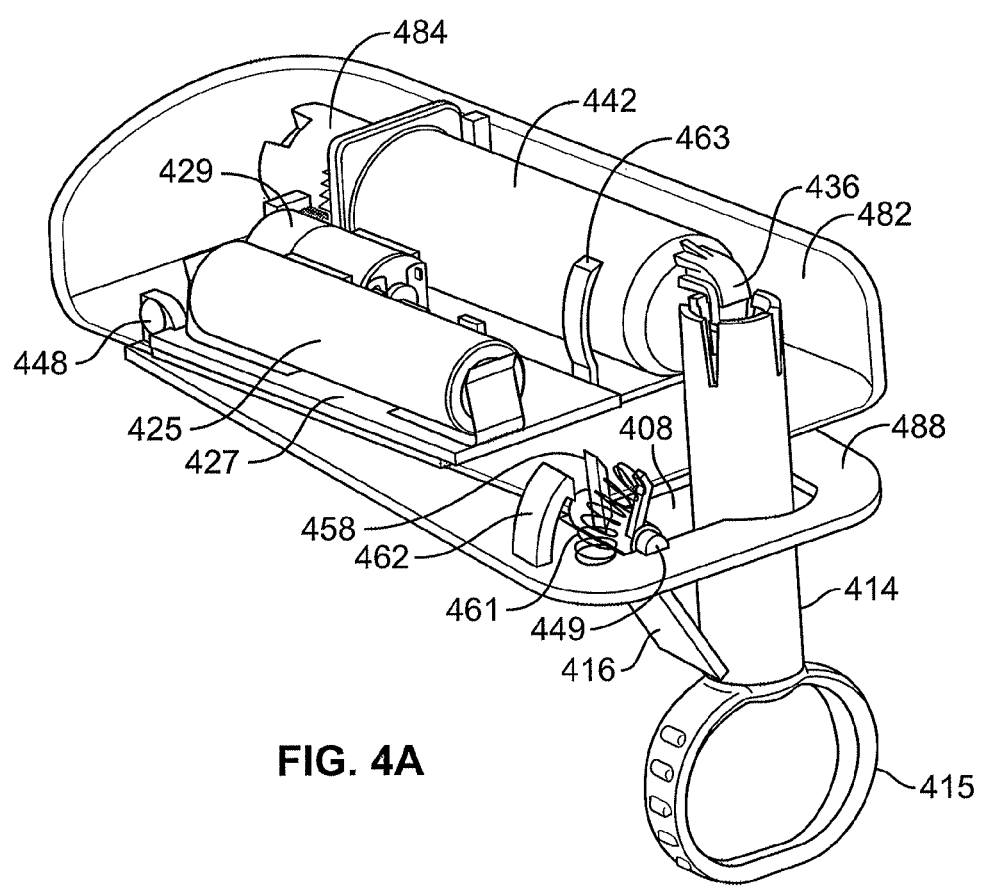
Figure 4C:
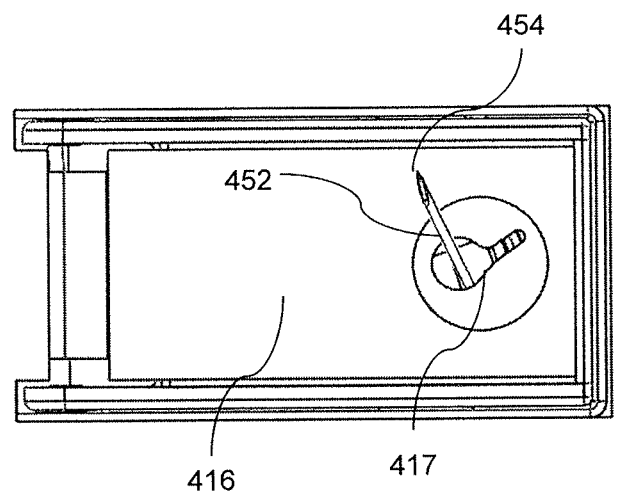
Figure 4D:
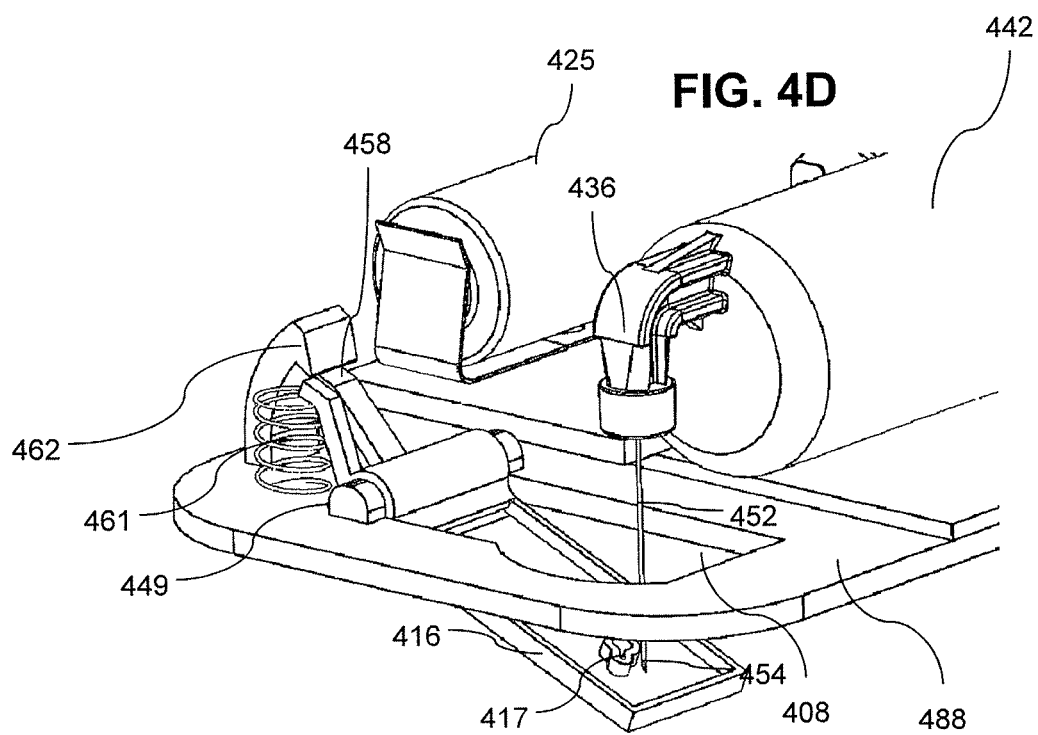

FIGS. 4A-4E are perspective views of a drug delivery device with pivoting needle shield latch in accordance with an embodiment of the current invention. In some embodiments, a needle shield may have a fully open state (for example as illustrated in FIGS. 4A, 4B and 5B) wherein the needle shield is opened far enough out of the way of device aperture as to allow a needle cap and/or a needle cap remover to extend out of the aperture. In some embodiments, a needle shield may have a shielding state (for example as illustrated in FIGS. 4D and 4E) wherein the needle shield for example prevents exposure of needle tip 454. In some embodiments, a needle shield may have a primed state (for example as illustrated in FIG. 4C) wherein the needle shield is positioned to allow a needle cap tip 454 to extend out of the device.

In some embodiments, shield/sensor 416 in some states may be included as a portion a skin contact surface of the device. Optionally, in the primed state, an outer surface of shield/sensor 416 is flush an outer surface of base 488. For example, in the primed state, the outer surfaces of shield/sensor 416 and/or base 488 form a skin contact surface of the device.

In some embodiments, a drug delivery device may include power source, for example including a battery 425. In some embodiments, a drug delivery device may include an actuator, for example including DC motor 429. In some embodiments, a drug delivery device may include a transmission, for example including a plunger driver 484. In some embodiments, a drug delivery device may include circuitry, for example a printed circuit board PCB 427. For example, circuit board 427 may electrically connect a power source to a status indicator and/or actuator according to an operational program. When the power source is electrically connected to motor 429, motor 429 optionally rotates transmission 484 driving a plunger and/or discharging a drug. Optionally, PCB 427 may include a processor and/or may be sensitive to one or more sensors. Alternatively or additionally, PCB 427 may function by a simple order of physical switches. Optionally a medicine cartridge may be installed into the device (for example preinstalled and/or installed by a user). In some embodiments the cartridge may in include barrel 442 optionally containing a drug and/or plugged at a proximal location with a plunger seal and/or having a hub 436 and/or needle 452 protected by a needle cap 404. Optionally plunger driver 484 may also be a part of a cartridge. Alternatively or additionally plunger driver 484 may be part of the delivery device.

FIGS. 4A and 4B illustrate an exemplary drug delivery device with a pivoting latch which is a needle shield 416 in an open position. In some embodiments, in the open position, needle shield 416 is excessively pivoted around a pivot 449 for example at an angle ranging between 75 and 90 and/or at an angle ranging between 75 to 50 and/or at an angle ranging between 50 to 30 degrees to a skin contact surface on the base 488 of the device.

In some embodiments, while needle latch 416 is in the opening position a needle cover and/or a cover remover 414 surround the needle 452 (for example needle 452 is illustrated in FIG. 4E). For example, the cap may seal around a portion of needle 452 protecting sterility of the needle and/or protecting the needle from contamination. Alternatively or additionally, a cap may protect a needle from physical damage and/or from causing damage to people and/or other objects. Optionally, the needle cover and/or cover remover 414 may inhibited needle latch 416 from moving to the shielding position and/or primed position. For example, cover remover 414 blocks and/or interferes with movement of shield 416 from the open position to the shielding position. In some embodiments, shield 416 may be biased to a shielding position. For example a spring 461 may bias shield 416.

Figure 8A:
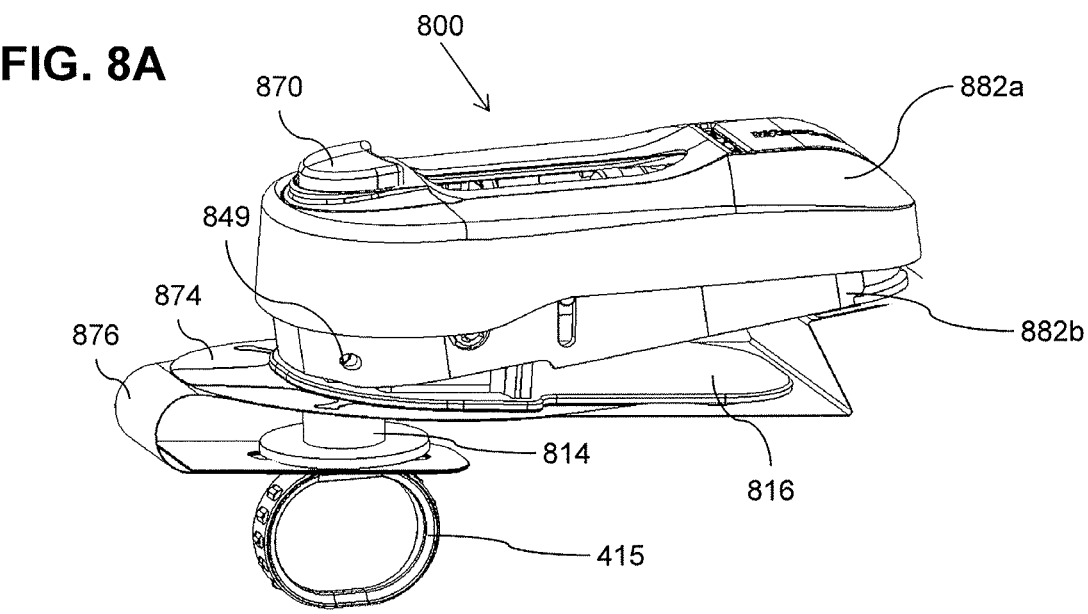
FIGS. 8A-8E are perspective views of drug delivery device with a skin sensor in accordance with an embodiment of the current invention.

In some embodiments, a user may activate the delivery device by pulling needle cap remover 414 away from base 488. For example pulling needle cap remover 414 may remove a needle cap (for example cap 404) from the cartridge and/or may peel an adhesive protector from base 488. For example, cap remover 414 may include a handle 415 (for example a pull ring) to facilitate removal by a user. Optionally, when needle cap remover 414 and/or needle cap 404 are removed, needle shield 416 may swing into a shielding position while mount 482 and/or needle tip 454 remain in the retracted state (for example a retracted state is illustrated in FIG. 8A and a needle shield in a shielding state is illustrated in FIG. 4D). Optionally, removing needle cap remover and/or removing needle cap 404 and/or pivoting of needle shield 416 into the shielding position may trigger a switch, remove a battery insulator and/or trigger a sensor to activate the delivery device and/or a user indicator and/or a processor. For example, in the shielding state, a needle shield may be at an angle ranging between 20 and 30 degrees to base 488 and/or between 10 and 20 degrees and/or between 5 and 10 degrees and/or between 30 and 50 degrees. In some embodiments, barrel 442 is held to the device by a clip 463.

In some embodiments, when the device is activated and/or needle 452 is retracted and/or needle shield 416 is in the shielding position, base 488 may be placed against the skin of a subject. Placing base 488 against the skin of a subject optionally pushes shield 416 in the dorsal direction up against base 488 and/or into an aperture 408 in base 488. For example shield 416 may move from the shielding position to a primed position (for example shield 416 is illustrated in a primed position in FIG. 4C). In the primed position a opening 417 in shield 416 may be aligned with needle tip 454. Optionally, when shield 416 is in the primed position and base 488 is against the skin of the subject, moving mount 482 and/or barrel 442 and/or needle tip 454 to the extended state causes needle tip 454 to extend out of opening 417 into the subject. For example, a needle may be extended by rotating around a pivot 448. Optionally while needle tip 454 is in the subject a drug is discharged into the subject.

In some embodiments, after the beginning of discharge, when the device is removed from the skin of a subject (for example after discharge is completed and/or upon a malfunction and/or by mistake) shield 416 pivots back to the shielding state (as illustrated in for example in FIG. 4D). Optionally, in the shielding position, shield 416 is prevented from returning to the open position by a latch 462 and/or a lock. For example, when shield 416 has moved to the shielding position and/or the retracted state and/or the primed state, latch 462 locks onto an appendage 548 of shield 416.

In some embodiments, a needle shield may be connected to multiple biasing elements. For example, spring 461 biases shield 416 to the shield and/or primed position (for example towards base 488). Additionally or alternatively, there may be a second biasing element (for example a leaf spring and/or latch 462 and/or a coil spring in the path of appendage 458). The second biasing element optionally engages shield 416 after it is prevented from returning to the open position (for example after appendage 458 is locked under latch 562). Optionally, the second biasing element biases shield away from base 488, for example to the shielding position.

In some embodiments, pivot 449 is a switch that enables needle tip 454 to advance through opening 417. For example, shield 416 is biased outward to a shielding position. An inward pressure against shield 416 causes shield 416 to rotate around pivot 449 to the primed position and/or enables needle tip 454 to pass through opening 417.

In some embodiments, when shield 416 is in the shielding position, opening 417 is not aligned with needle tip 454 and/or exposure of needle tip 454 prevented by shield 416. Optionally when shield 416 is in the shielding position and/or the primed position it completely and/or partially blocks aperture 408 and/or prevents replacing needle cap 404 and/or cap remover 414. Alternatively or additionally, when shield 416 returns to the shielding position (for example after being in the primed position) a switch and/or sensor may be triggered setting the device into a post injection state and/or inactivating the device and/or stopping discharge (for example if the device was removed prematurely) and/or activating a warning (for example if the device malfunctioned and/or was removed prematurely). In some embodiment, when needle 452 is extended, shield 416 is prevented from returning to the primed position.

Figure 5A:
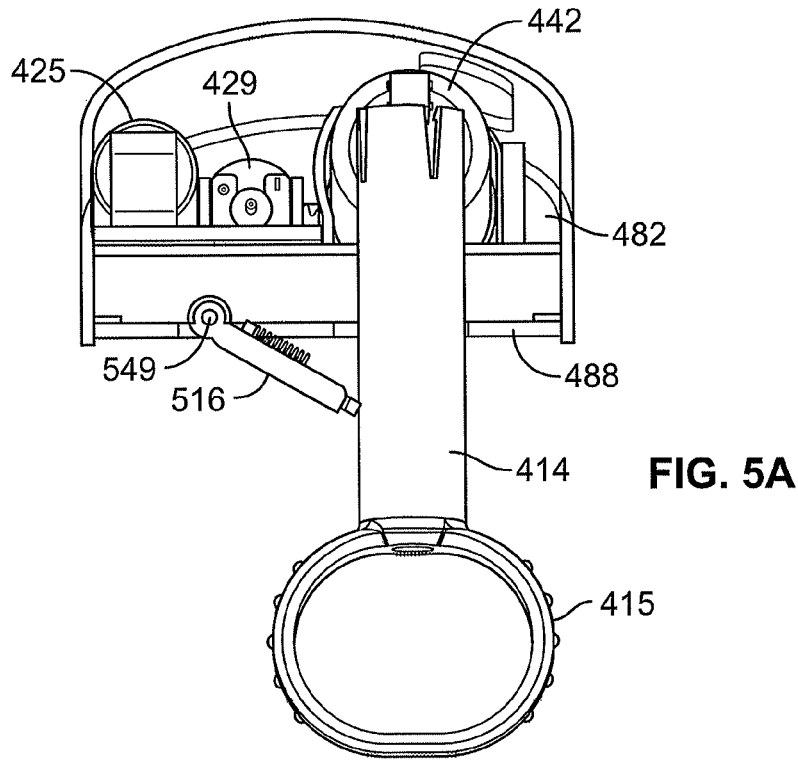
FIGS. 5A-5B are perspective views of an extending needle shield latch in accordance with an embodiment of the current invention.
Figure 5B:
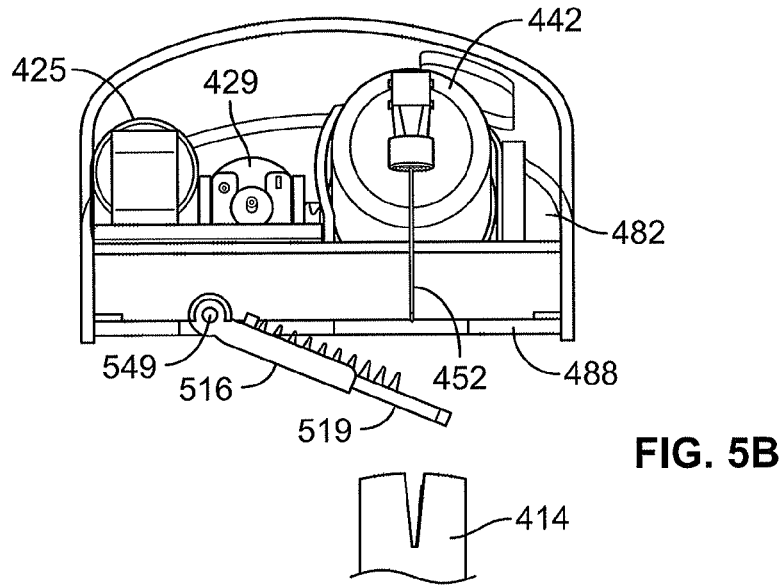

FIGS. 5A and 5B are perspective views of a drug delivery device with an extending latch which is an extending needle shield 516 in accordance with an embodiment of the current invention. In some embodiment in the open position (for example as illustrated in FIG. 5A) needle shield 516 is not excessively pivoted around a pivot 549. Optionally the angle between shield 516 and the skin contact surface of base 488 in the shielding position and the open position are the same. Shield 516 optionally moves from the open to the shielding state by extending an extension 519 into an extension path of the needle and/or a path of the needle cap and/or path of the needle and/or a path of the needle cap remover. Once extension 519 has been extended, it may lock in position and/or prevent exposure of a needle and/or prevent replacing a needle cap and/or prevent replacing needle cap remover 414. Optionally shield 516 has a primed position which allows needle extension. For example, with extension 519 extended, shield 516 may be pushed toward base 488 to the primed position in which a opening is aligned a needle. In some embodiments, with extension 519 in the extended position, shield 516 may have the same geometry and/or functionality as described above for example with respect to shield 416 (for example in FIGS. 4A-4D and their accompanying description).

Movement of a Needle and/or a Needle Cap

FIGS. 6A-6D are schematic illustrations of an injector having a non-linear movement and a shield in accordance with an embodiment of the present invention. In some embodiments a needle shield and/or sensor may interfere with movement of a needle and/or a needle cover.

In some embodiments, a trajectory of movement may be linear (for example as a needle 652 and/or cap 604 move the longitudinal axis may remain unchanged) or curved (for example as needle 652 and/or cap 604 move the direction of the longitudinal axis may change). In some embodiments, the trajectories of cap 604 and/or needle 652 may coincide and/or they may differ.

In some embodiments, a first object (for example a needle shield and/or sensor) may interfere with movement of a second object (for example a needle and/or a cap) by occupying a space to which the object is moving [for example in FIG. 5A cap remover 414 occupies the space to which shield extension 519 moves in a shielding state for example as illustrated in FIG. 5B]. Alternatively or additionally, a first object (for example a needle shield and/or sensor) may interfere with movement of a second object (for example a needle and/or a cap) by blocking a trajectory of movement. For example, in FIG. 6A a shield 616 in a shielding position blocks a trajectory for removal of cap 604.

FIG. 6A illustrates an embodiment of an injector in a non activated state in accordance with an embodiment of the current invention. In some embodiments, an injector includes a drug reservoir 642 in fluid communication with a hollow needle 652 (for example as illustrated in FIG. 6B). Optionally, the injector is supplied to a user in a non activated state. For example, in the non activated state needle 652 may be covered by a cap 604. Optionally needle 652 and/or cap 604 may be straight and/or axially symmetric. For example, in the covered state, needle 652 and cap 604 are coaxial. Optionally, the injector includes a needle shield 616 initially in a shielding position. In shielding position, the shield 616 optionally blocks an open end (e.g. the lower face) of an injection zone 691 (illustrated as a dashed box in FIGS. 6A-6D.

FIGS. 6B and 6C illustrate an injector in an activated state in accordance with an embodiment of the current invention. For example, a user may activate an injector by moving shield 616 to an active position (for example as illustrated in FIG. 6B). For example, shield 616 may be rotated around a pivot 648 to the active position. Optionally, in the active position, shield 616 may clear injection zone 691 and/or a clear a path 693 (for example illustrated by the dashed arrow in FIG. 6B) for removal of needle cap 604. For example, trajectory 693 may be straight and/or parallel and/or coaxial with the longitudinal axis of needle 652. Optionally trajectory 693 passes through injection zone 691. In some embodiments, in the shielding position (for example as illustrated in FIG. 6A), shield 616 blocks trajectory 693 and/or interferes with removal of cap 604.

In some embodiments, needle 652 may be inserted into injection zone 691. Optionally, a trajectory 694 of the sharp tip of the needle (for example illustrated by the dashed line in FIG. 6C) may not be along a straight line. For example, needle 652 may be inserted into injection zone 691 by rotating around a pivot 648. Optionally, the tip of needle 652 follows a curved trajectory 694, for example an arc.

FIG. 6D illustrates an injector in a locked state after injection in accordance with an embodiment of the current invention. In some embodiments, needle shield 616 may be returned to the shielding state, for example at the end of drug discharge and/or when the injector in removed from an injection location. For example the shield may be returned to the shielding state to protect needle 652 from a stick hazard.

FIGS. 7A-7D are schematic illustrations of an injector having a linear movement and a shield in accordance with an embodiment of the present injections. In some embodiments a needle shield and/or sensor may interfere with movement of a needle and/or a needle cover.

Figure 7A:
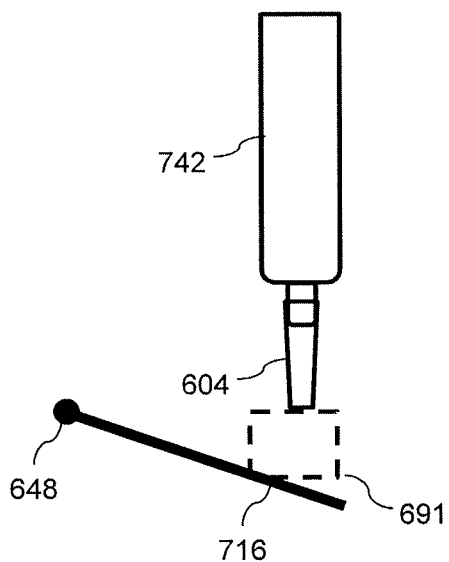
FIGS. 7A-7D are schematic illustrations of an injector having a linear movement and a shield in accordance with an embodiment of the present injections.
Figure 7B:
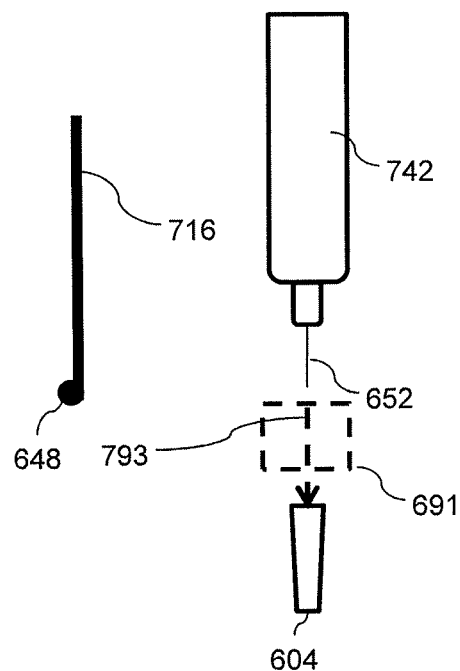

FIG. 7A illustrates an embodiment of an injector in a non activated state in accordance with an embodiment of the current invention. In some embodiments, an injector includes a drug reservoir 742 in fluid communication with a hollow needle 652 (for example as illustrated in FIG. 7B). Optionally, the injector is supplied to a user in a non activated state. Optionally, the injector includes a needle shield 716 initially in a shielding position. In shielding position, the shield 716 optionally blocks an open end (e.g. the lower face) of an injection zone 691 (for example as illustrated by the dashed box in FIGS. 7A-7D).

Figure 7C:
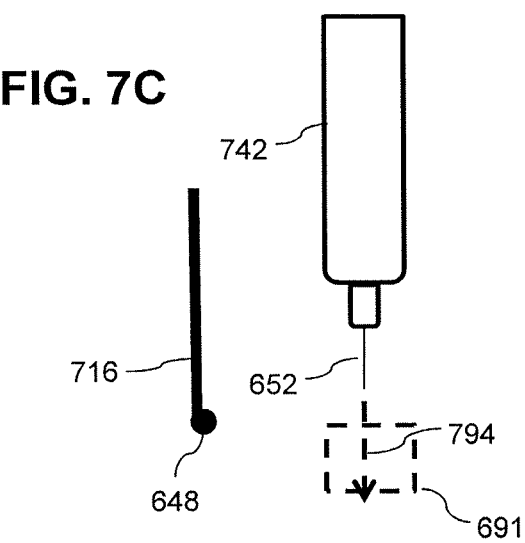

FIGS. 7B and 7C illustrate an injector in an activated state in accordance with an embodiment of the current invention. For example, a user may activate an injector by moving shield 716 to an active position (for example as illustrated in FIG. 7B). For example, shield 716 may be rotated around a pivot 648 to the active position. Optionally, in the active position, shield 716 may clear injection zone 691 and/or a trajectory 793 (for example illustrated by the dashed arrow in FIG. 7B) for removal of needle cap 604.

In some embodiments, needle 652 may be inserted into injection zone 691. Optionally, a trajectory 794 of the sharp tip of the needle (for example illustrated by the dashed line in FIG. 7C) may not be along a straight line. In some embodiments, needle 652 is rigidly connected to reservoir 742 and/or moves with reservoir 742. Alternatively or additionally, a needle may be connected to a reservoir by a flexible member and/or joint and/or may move independently of the reservoir. For example, a needle may be connected to a reservoir by a flexible tube.

Figure 7D:
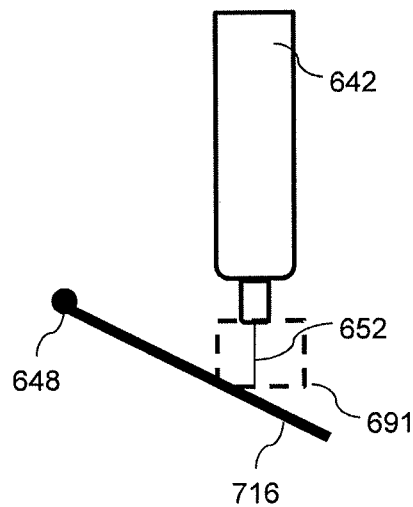

FIG. 7D illustrates an injector in a locked state after injection in accordance with an embodiment of the current invention. In some embodiments, in the locked state, needle shield 716 may be returned to the shielding state, for example to protect needle 652 from a stick hazard.

FIGS. 8A-8E illustrate an injector with a sensor in accordance with an embodiment of the current invention. In some embodiments, a state of an injector may be switched according to a state of a sensor. Optionally, the sensor interacts with a needle cap. For example, a skin sensor may be stimulated and/or moved when an injector is placed on the skin of a user. The needle cap may block stimulation of the sensor and/or interfere with movement of the sensor.

Figure 8B:
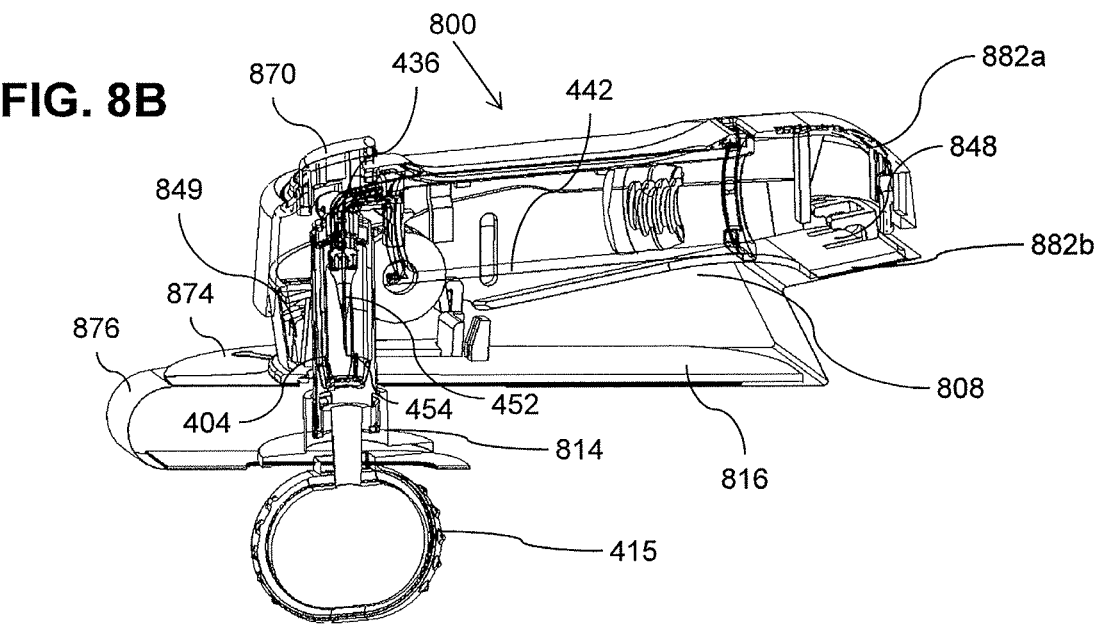

FIGS. 8A and 8B are perspective and cross sectional views (respectively) of an injector in an initial state in accordance with an embodiment of the current invention. Optionally in the initial state, the device is not activated. In some embodiments, an injector 800 may include one or more cap puller 814 that interfere with movement of a skin sensor 816. For example, in the non activated state, sensor 816 may be extended away from a top housing 882a and/or a lower housing 882b of injector 800. Optionally, injector 800 is primed and/or activated by collapsing sensor 816 toward housing 882*a*, 882*b*. In some embodiments, cap puller 814 interferes with movement of sensor 816 towards housing 882*a*, 882*b*.

In some embodiments, sensor 816 moves towards housing 882*a*, 882*b* by rotating around a pivot 849. Puller 814 optionally fits to sensor 816 such that rotation of sensor 816 moves puller 814. In turn, puller 814 is optionally rigidly attached to a needle cap 404 and/or a needle 452 and/or a neck 436 of a reservoir 442 and/or housing 882*a* which may inhibit movement of puller 814. Inhibiting movement of puller 814 optionally inhibits rotation of sensor 816 and/or inhibits activation, priming and/or user of injector 800.

In some embodiments, cap 404 and/or puller 814 may move longitudinally with respect to sensor 816, for example along an axis of needle 452. For example, cap 404 and/or puller 814 may fit through a opening (for example opening 817 of FIG. 8C) in sensor 816. Optionally, cap 404 and/or puller 814 are removed by linear movement away from the device. Optionally, removing cap 404 and/or puller 814 from injector 800 may facilitate activation and/or priming of the device. In some embodiments, cap puller 814 may be connected to a handle, for example a pull ring 415. The handle may facilitate a user removing puller 814 and/or cap 404.

In some embodiment sensor may include a skin contact surface. Optionally a skin contact surface may include an adhesive 874. For example, adhesive 874 may attach sensor 816 to the skin of a user in the vicinity of an injection site. Optionally, handle 415 and/or pull ring 814 and/or cap 404 is attached to an adhesive liner 876 such that removing cap 404 peels liner 876 from adhesive 874. In some embodiments, housing 882*b*, 882*b* may include a skin contact surface and/or an adhesive. Liner 876 may also protect the adhesive of the housing 882*a*, 882*b* and/or be peeled off housing 882*a*, 882*b* with removal of cap 404. Alternatively or additionally, a switch and/or battery isolator may be attached to handle 415 and/or pull ring 814 and/or cap 404 such that removing cap 404 removes the battery isolator and/or triggers the switch.

Figure 8C:
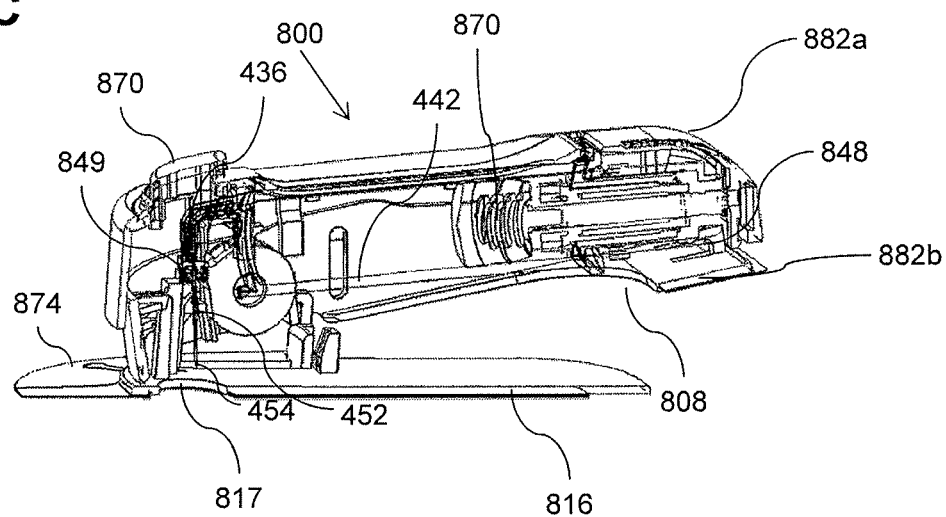

FIG. 8C is a cross sectional illustration of an injector with a needle cap removed in accordance with an embodiment of the current invention. In some embodiments, removing the needle cap includes peeling a liner off an adhesive surface (for example a skin contact surface). Optionally, removal of needle cap 404 may activate the injector 800. For example, a CPU may be started and/or self tests and/or timers may be initiated. For example, in FIG. 8C, in the activated state, sensor 816 is deployed away from housing 882*b*. Optionally sensor 816 is interlinked to an activation switch. For example an activation switch may include a needle insertion button 870. For example, when sensor 816 is in the deployed state needle insertion button is locked and/or needle insertion is inhibited.

Figure 8D:
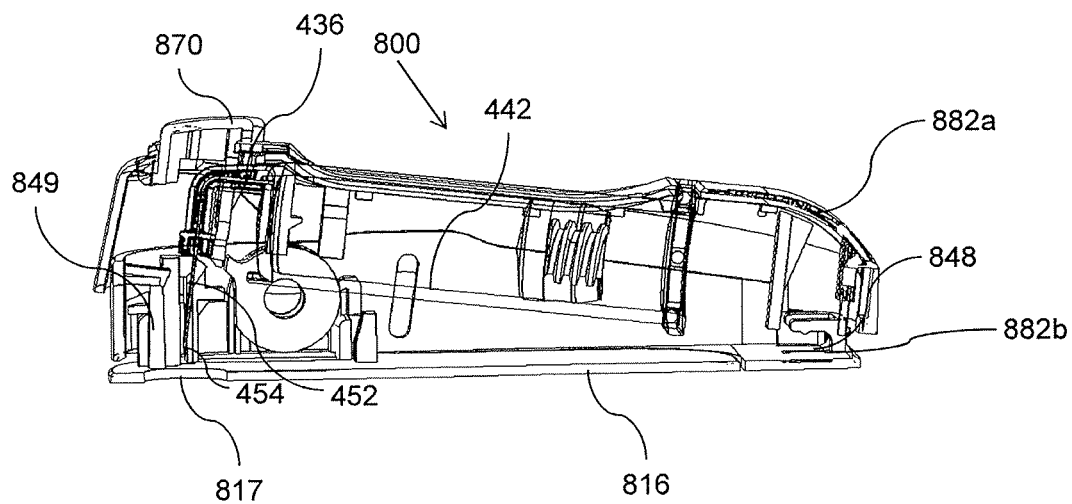

FIG. 8D is a cross sectional illustration of an injector with a skin sensor in a collapsed state in accordance with an embodiment of the current invention. In some embodiments, injector 800 may be primed by collapsing sensor 816 towards housing 882*b* and/or into aperture 808. For example, sensor 816 may be collapsed by placing sensor 816 against an injection site (for example on the skin of a user) and/or adhering sensor 816 to the injection site and/or pushing housing 882*a*, 882*b* towards sensor 816 and/or towards the injection site. Optionally the device is primed when sensor 816 collapses. Optionally, when the device is primed, needle insertion switch 870 is unlocked, allowing and/or facilitating needle insertion. Alternatively or additionally, collapsing of sensor 816 may trigger needle insertion.

Figure 8E:
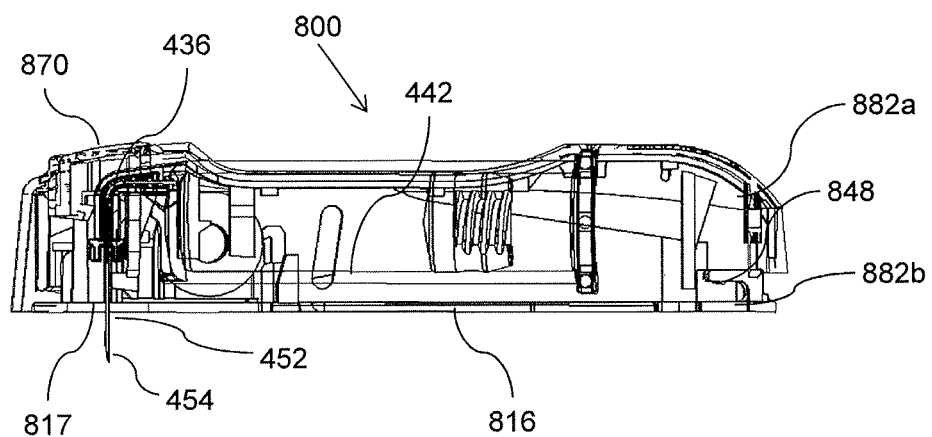

FIG. 8E is a cross sectional illustration of an injector in an active state in accordance with an embodiment of the current invention. For example, while injector 800 is in a primed state, a user may depress needle insertion button 870. Depressing button 870 optionally triggers an insertion driver. For example, the driver may cause upper housing 882*a* to rotate around pivot 848 with respect to lower housing. Rotation may insert needle tip 454 through aperture 808 in housing 882*b* and/or through opening 817 in sensor 816 into an injection zone of a skin of the user. Alternatively or additionally a needle may be inserted by a linear motion. Alternatively or additionally a needle insertion driver may be triggered directly by collapse of sensor 816. Alternatively or additionally, needle insertion may be manual (for example the pressure that the user puts onto button 870 and/or upper housing 882*a* may push needle tip 454 into the skin.

In some embodiments, needle tip 454 may be protected after drug delivery and/or upon removal of device 808 from the skin of a user. For example needle 452 may be retracted into housing 882*a*, 882*b* and/or a needle shield may be deployed to shield needle tip 454.

In some embodiments, in some states, sensor 816 is flush with a base of the device and/or forms a part of a skin contact surface of the device. Optionally in the collapsed state the outer surface sensor 816 is flush with lower housing 882*b*. For example the outer surface of sensor 816 and lower housing 882*b* may form a skin contact surface of the device.

In some embodiments, pivot 849 is a switch that enables needle tip 454 to advance through opening 817. For example, shield 816 is biased outward to a shielding position. An inward pressure against shield 816 causes shield 816 to rotate around pivot 849 to the primed position and/or enables needle tip 854 to pass through opening 817.

Figure 9A:
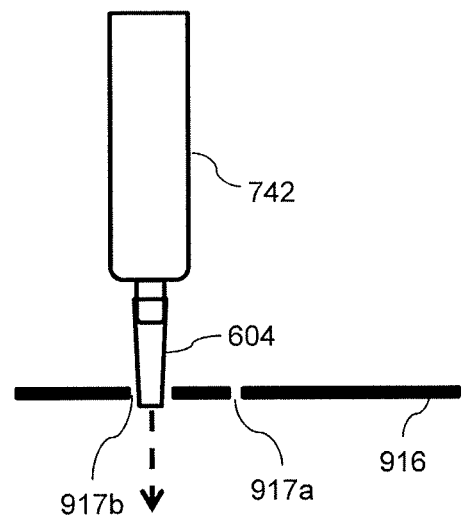
FIGS. 9A-9C are schematic views of drug delivery device with a shield in accordance with an embodiment of the current invention.
Figure 9B:
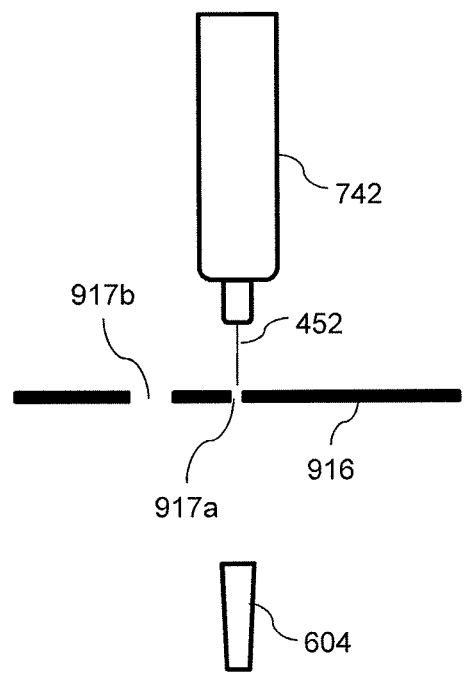
Figure 9C:
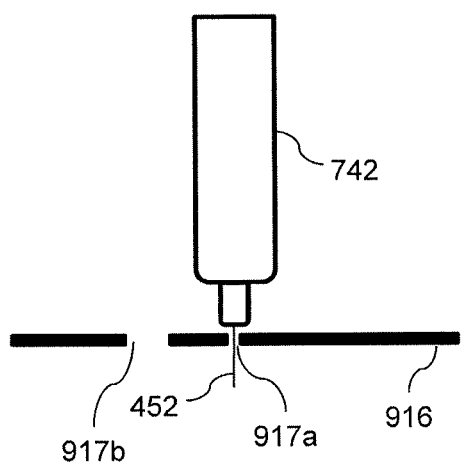

FIGS. 9A-9C are schematic illustrations of a needle shield in accordance with an embodiment of the current invention. In some embodiments, a needle shield may move linearly with respect to an injection needle. Optionally, a needle cap may interfere with movement of the needle shield. For example removing the needle cap may allow, facilitate and/or trigger movement of the shield. In some embodiments, a needle shield may include a large opening sized and shaped for a needle cap to pass therethrough. Alternatively or additionally, when the needle cap is on the needle, the shield maybe moved aside and/or the needle cap may pass by an edge of the shield. In some embodiments a needle cap may include a small opening shaped and sized for a needle to pass therethrough.

FIG. 9A illustrates a schematic view of an injector with a needle protected by a needle cover in accordance with an embodiment of the current invention. In some embodiments, a needle cover 604 and/or a cover remover protecting a needle of an injector device may protrude through an aperture 917*b* in a needle shield 916 of the device. For example, aperture 917*b* may be sized to allow cover 604 to pass therethrough. For example, cover 604 may pass therethough by translating linearly along a longitudinal axis of cover 604 and/or needle 452 (as illustrated for example in FIG. 9B). Optionally, in the protecting position, cover 604 and/or the cover remover interferes with movement of shield 916.

In some embodiments shield 916 may be freed by pulling needle cover 604 may away from the injector. For example, cover 604 may be pulled away from the injector in the direction of the arrow in FIG. 9A.

FIG. 9B illustrates a schematic view of an injector with a needle cap removed in accordance with an embodiment of the current invention. Optionally, when cap 604 is removed, shield 916 is free to translate. For example, comparing FIG. 9A to FIG. 9B it can be seen that shield 916 has translated sideways so that a smaller aperture 917a becomes aligned with needle 452 and/or the larger aperture 917b is no longer aligned with the axis of needle 452. Optionally aperture 917a is large enough for needle 452 to pass therethrough, but too small for cap 604 to pass therethrough.

FIG. 9B illustrates a schematic view of an injector in an active state in accordance with an embodiment of the current invention. For example, in the active state, needle 452 extends out of aperture 917a. Optionally the outer surface of shield 916 includes a skin contact surface and/or an adhesive to adhere to an injection zone of the user. For example, needle 452 may project into the skin of the user and/or a drug may be discharged under the skin.

In some embodiments, after discharge of a drug needle 452 may be protected. For example reservoir 742 and/or needle 452 may be retracted behind shield 916 (e.g. above shield 916 in the FIG. 9C). Alternatively or additionally, shield 916 may move outward (e.g. linearly and/or by rotation) to shield needle 452.

Exemplary Dimensions of a Drug Delivery Device

In some embodiments the payload of a reservoir (for example a syringe) may include, for example between 0.5 and 2 ml and/or between 2 and 4 ml and/or between 4 and 6 ml and/or between 4 and 10 ml of a drug and/or more. In some embodiments, the injector may discharge the entire payload as a single dose. A drug delivery device may include, for example, a patch injector, and/or an internally powered driver to drive the plunger and/or discharge the payload. For the sake of this application an internally powered injector driver may be defined as a drive mechanism powered by energy stored at least temporarily within the injector. Power may be stored in a power supply, for instance as chemical potential (for example a chemical that produces an expanding gas and/or a battery) and/or mechanical potential (for example stored in an elastic member and/or a spring and/or a pressurized gas). For example the driver may be designed to discharge the payload over a time period ranging between 20 and 120 seconds and/or between 120 and 600 seconds and/or between 600 seconds and an hour and/or between an hour and a day and/or longer.

In some embodiments of an injector, a needle is inserted into a subject by rotating a cartridge rigidly connected to the needle. Optionally a dual movement pivoting assembly keeps the needle insertion point stationary in the plane of the base of the device. For example, a pivot element may slide while pivoting thereby keeping the insertion location on the skin of the patient stationary. Alternatively or additionally the dual movement pivot may include a cam and/or an extending lever arm. For example the pivoting movement may be over an angle of 7 to 9 degrees and/or 4 to 7 degrees and/or 2 to 4 degrees and/or 9 to 15 degrees and/or 15 to 30 degrees. The sliding movement may optionally offset horizontal movement of the needle puncture location in the plane of the skin of the subject due to rotation. For example, horizontal movement of a needle may generate a load over the needle that may cause a leak around the insertion area. Optionally, a dual movement pivoting assembly will inhibit the horizontal movement of the needle and/or the insertion location and/or alleviated the load on the needle. Optionally the longitudinal movement of a needle may range between 7.5 to 8 mm and/or between 6 to 7.5 mm and/or between 2 and 6 mm and/or between 8 to 10 mm and/or between 10 to 15 mm and/or between 15 to 50 mm. In some embodiments, the horizontal movement of the needle insertion may for example range between 0 to 0.4 mm and/or 0.4 to 0.8 mm and/or 0.8 to 2 mm. Horizontal movement of the dual movement pivoting assembly, for example lengthening of cam arm and/or sliding of a pivot point optionally compensates for the horizontal movement. For example the horizontal movement of the dual movement pivoting assembly may be of the same order as the horizontal movement of the needle insertion location, for example ranging between 0 to 0.4 mm and/or 0.4 to 0.8 mm and/or 0.8 to 2 mm. Various mechanisms may be used to keep the needle insertion location stationary in spirit with the invention, for example and extending arm and/or an extending mount and/or an extending lever and/or a track (for example a linear track) and/or a cam.

In some embodiments, the apparatus may be preprogrammed to wait a fixed time delay ranging between 2 to 20 minutes and/or 20 minutes to an hour and/or an hour to 6 hours and/or 6 hours to 2 days after activation before beginning delivery of the substance. Optionally the length of the time delay may be an estimated time for a temperature sensitive component of the apparatus to reach a preferred working temperature. For example, the temperature sensitive component may include the drug and/or a battery.

In some embodiments, discharge may be driven by a driver. An internally powered driver may be powered by various mechanisms including for example a motor (including for example a DC motor, an actuator, a brushless motor) and/or a transmission including for example a telescoping assembly and/or a threaded element and/or a gear and/or a coupling and/or an elastic mechanism (for example a spring and/or a rubber band) and/or an expanding gas and/or a hydraulic actuator).

A drug delivery device in accordance with some embodiments of the current invention may include reservoir. For example a reservoir may include a medicine container and/or a syringe. Optionally a syringe may be preloaded with medicine using standard equipment and/or in an aseptic room. A preloaded syringe may optionally include a proximal opening. A plunger may optionally seal the proximal opening and/or protect the sterility of the contents of the syringe. A sterile needle (for example a hollow needle) may optionally be connected to the syringe barrel. For example, the hollow of the needle may be in fluid communication with the interior of the barrel. The needle may optionally be rigidly attached to the hub at the distal end of the barrel. The sterility of all and/or part of the needle may for example be protected by a sterile cover. The sterile cover may remain on the needle when the syringe is supplied and/or installed into an injector. For example, the medicine container may optionally include a cylindrical barrel rigidly attached to a needle. In some embodiments a plunger may slide axially along the inside of the barrel to discharge a medicine payload. For example, the medicine may be discharged through the hollow needle. The protruding tip of the needle may be oriented at an angle to the axis of the barrel.

An aspect ratio of the base may be defined as the ratio of the length of the longest axis of the base to the shortest axis. Optionally the axis ratio may range between 1 to 1.5 and/or 1.5 to 2 and/or between 2 to 3 and/or greater than 3. In some embodiments, the height of the injector may range between half the length of the short axis of the base to the length of the short axis of the base and/or between the length of the short axis of the base to twice the length of the short axis of the base and/or greater than the twice length of the short axis of the base. The height of the injector may supply leverage for pivoting the adhesive off the skin of a patient after use.

In some embodiments, the force to insert the needle to the skin of a patient may range for example between 0.02 to 0.2 N and/or between 0.2 and 0.5 N and/or between 0.5 to 5 N. Optionally, the force required to inject the drug (for example the force on a syringe plunger) may range for example between 5 to 60 N. For example the force required to inject the drug may depend on the injection rate and/or the viscosity of the drug and/or the syringe geometry and/or the needle dimensions.

In some embodiments a needle protection mechanism may be triggered by a linear force greater than, for example, between 10 to 60 N.

For example, drug delivery device may include an auto-injector. The auto-injector may be activated by manually pushing with enough force to insert the needle. The device may then apply an injection force to inject a drug. Once the entire drug is injected and/or when there is an obstruction and/or occlusion, the injection force may rise until it passes a threshold triggering safeguarding of the needle and/or ending injection.

For example in the event of an occlusion and/or at the end of delivery, the linear force generated by the device may increase to the level of up to 60 N. A needle safeguarding mechanism (for example a needle retraction mechanism) may be sensitive to the force. For example mechanism may include a snap that gives way at 40 N returning the needle to the retracted position.

In some embodiments, the stress to inject a medicine and/or to trigger safeguarding of a needle may include a torque. For example, injection of medicine may be driven by a plunger. The plunger may optionally be driven by a threaded assembly, for example a threaded screw and/or teeth and/or a telescoping assembly. Optionally the pitch of the teeth and/or an associated screw may range for example between 0.5 and 2 mm. The diameter of the screw may range for example between 2.5 and 15 mm. The torque to power injection may range for example between 0.2 and 1.0 N*cm. The trigger torque (the torque at which the needle safeguarding is triggered) may range for example between to 0.5 to 2 and/or from 2 to 4 and/or from 4 to 10 N*cm.

In some embodiments a safety mechanism may include linear movement of the ranging between 5 to 15 mm. For example movement of the safety mechanism may include extension of a needle during insertion and/or retraction of the needle and/or extensions of a safety shield and/or retraction of a safety shield. Optionally a needle insertion length (for example the length of needle inserted into a patient) may range for example between 3 to 12 mm.

During injection, the linear movement of a plunger may range for example between 10-50 mm. The length of movement of the plunger may vary for example with the volume of medicine to be injected that may range for example between 0.5 to 3 ml.

In some embodiments, a safeguarding mechanism may be sensitive to a torque. For example, the needle may be retracted when the mechanism is exposed to a twisting moment. Optionally, discharge may be driven by a torque. For example the driver may apply torque to threaded element pushing a plunger. When the torque on the driver reaches a threshold value, the needle may be released and/or retracted and/or a needle shield may be deployed. Alternatively or additionally the trigger mechanism may require both a torque and a linear force. For example, requiring both a torque and a linear stress may prevent premature activation due to momentary friction.

In some embodiments a time of discharge may range may depend on the fill volume and/or viscosity For example the expected injection speeds may be Injection speed depend on viscosity, for example for viscosity ranging from 1 cp to 15 cp the expected injection rage may range between 30 to 40 sec/1 ml, for example for viscosity ranging from 15 cp to 60 cp the expected injection rate may range between 35 to 60 sec/ml for viscosity above 60 cp the expected injection rate may range between 53 to 67 sec/lml. The maximum and/or minimum expected injection time may for example be the maximum and/or minimum allowed fill volume divided by an injection rate. For example an expected time of discharge may range for example between 24 to 48 seconds (for example for between 0.8 and 1.2 ml of fluid having a viscosity ranging between 1 to 15 cp) and/or between 36 to 68 seconds (for example for between 1.2 and 1.7 ml of fluid having a viscosity ranging between 1 to 15 cp) and/or between 51 to 92 seconds (for example for between 1.7 and 2.3 ml of fluid having a viscosity between 1 to 15 cp) and/or between 70 to 150 seconds (for example for 2.0 to 2.5 ml of fluid having a viscosity of between 15 and 40 cp) and/or between 120 seconds and 3 minutes for larger volumes and/or viscosities. In some embodiments injection times may be longer. The length of the injection time may be determined by considerations other than viscosity and/or volume.

In some embodiments reservoir may have a length ranging for example between 20 to 42 and/or 42 to 48 mm and/or 48 to 80 mm and/or 80 to 200 mm. In some embodiments an internal cylindrical space of a reservoir may have an average width ranging for example between 1 to 3 mm and/or 3 to 10 and/or 10 to 15 mm and/or 15 to 25 mm and/or 25 to 50 mm. Optionally a reservoir may have a circular cross section such that width is the diameter of the circle. In some embodiments a hub may have a straight end portion with a length ranging for example between 1 to 3 mm and/or 3 go 7 mm and/or 7 and 8 and/or 8 to 10 mm and/or 10 to 15 mm and/or 15 to 50 mm. In some embodiments straight portion of a needle extending out of a hub may have a length ranging for example between 1 to 5 mm and/or 5 and 7 mm and/or 7 to 10 mm and/or 10 to 20 mm. In some embodiments hub may have sealing ring for a needle cap. The sealing ring may have a length ranging for example between 0.1 to 0.6 mm and/or 0.6 to 1 mm and/or 1 to 2.5 mm and/or 2.5 to 3 mm and/or 3 to 6 mm and/or 6 to 15 mm. In some embodiments sealing ring may have an internal cavity with a length ranging for example between 0.5 to 1.5 mm and/or 1.5 to 2.5 mm and/or 2.5 to 5 mm and/or 5 to 10 mm. In some embodiments sealing ring may have an external average width which also may be an average outer diameter ranging for example between 1 to 4 mm and/or 4 to 5 mm and/or 5 to 10 mm and/or 10 to 20 mm. In some embodiments sealing ring may have an internal average width which also may be an average inner diameter ranging for example between 1 to 3 mm and/or 3 to 4 mm and/or 4 to 10 mm and/or 10 to 18 mm. In some embodiments, a hub may have a neck (not including the sealing ring) with an average width which may be an average diameter ranging for example between 1 to 3 mm and/or 3 to 4 mm and/or 4 to 8 mm and/or 8 to 16 mm. Optionally the neck may have a non-uniform cross section (for example an I beam and/or cross shaped cross section) and/or a tapered cross section. For a non-uniform cross section that average outer width will be defined as the width of the smallest oval that can enclose the neck averaged over the length of the neck. In some embodiments a fluid path between a hub and a reservoir cavity may include a 27 gauge needle and/or a needle ranging between 25 to 30 gauge and/or a needle ranging between 20 to 25 gauge and/or a needle ranging between 30 to 32 gauge. In some embodiments a needle protruding from a hub may include a 27 gauge needle and/or a needle ranging between 25 to 30 gauge and/or a needle ranging between 20 to 25 gauge and/or a needle ranging between 30 to 32 gauge.

It is expected that during the life of a patent maturing from this application many relevant technologies and/or materials will be developed and the scope of the terms are intended to include all such new technologies and materials a priori.

As used herein the terms "about", "approximately" and "substantially" refer to ±5%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An injector with a needle stick protector comprising:
   a frame having a skin contact surface and defining an aperture in said skin contact surface;
   a needle having a sharp tip configured to advance through said aperture;
   a needle protector removably mounted over said needle; and
   a stick protector movably attached to said frame and biased against said needle protector, the stick protector being movable into a shielding position upon removal of the needle protector, blocking exposure of the sharp tip and preventing the needle from deploying.

2. The injector of claim 1, further including a handle for pulling said needle protector away from said needle thereby freeing said stick protector to move to the shielding position shielding said sharp tip of the needle.

3. The injector of claim 1, wherein said needle protector protrudes through said aperture.

4. The injector of claim 1, wherein said biasing causes said stick protector to overhang said aperture.

5. The injector of claim 1, further comprising:
   a pharmaceutical reservoir in fluid communication with said needle and having a long axis parallel to said skin contact surface.

6. The system of claim 5, wherein the needle is rigidly attached to said pharmaceutical reservoir.

7. The system of claim 6, wherein a longitudinal axis of the needle at the sharp tip thereof is oriented at an angle of between 30 to 150 degrees with respect to a long axis of said pharmaceutical reservoir.

8. The system of claim 7, wherein said pharmaceutical reservoir includes a cylindrical bore and said long axis is the longitudinal axis of the bore.

9. The system of claim 1, wherein said needle is sterile and said needle protector protects a sterility of the needle.

10. The system of claim 1, wherein said skin contact surface includes an adhesive.

11. A needle protection system for an autoinjector comprising:
    a frame including a skin contact surface having an aperture;
    a sterile needle including a sharp tip on a distal portion thereof, a connection between said needle and said frame defining a pathway of movement for advancing said tip through said aperture;
    a needle protector removably attached to said needle, said needle protector being removable from said needle along a trajectory defined by sliding of said needle protector along an axis of said distal portion of said needle; and
    a shield connected to said frame, the shield being movable between a deployed position blocking said pathway and said trajectory, an open position clearing said pathway and said trajectory and a primed position blocking said trajectory and clearing said pathway.

12. The system of claim 11, wherein said needle protector inhibits contamination of said sharp tip.

13. The system of claim 11, wherein said needle shield is coupled to said needle protector such that removing said needle protector causes said shield to move from said open position to said shielding position.

14. The system of claim 13, wherein said shield blocks replacement of said protector when said shield is in said shielding position.

15. The system of claim 11, further comprising:
a needle driver configured to control said advancing of said needle tip and wherein said shield is interconnected to said needle driver to prevent said advancing when said shield is in said shielding position.

16. The apparatus of claim 11, wherein said shield includes a latch that pivotally mounted to said frame.

17. The apparatus of claim 11, wherein said shield includes a needle opening large enough to allow said needle tip to pass therethrough but smaller than said aperture, wherein in said primed position said needle is aligned to pass through said needle opening.

18. The apparatus of claim 17, wherein in said shielding position said needle is misaligned with said needle opening.

19. The apparatus of any of claim 17, wherein in said primed position said shield is flush with said frame.

20. The needle protection system of claim 11, further comprising:
a pharmaceutical reservoir in fluid communication with said needle and having a long axis parallel to said skin contact surface.

21. The system of claim 20, wherein the sterile needle is rigidly attached to said pharmaceutical reservoir.

22. The system of claim 21, wherein a longitudinal axis of the needle at said sharp tip is oriented at an angle of between 30 to 150 degrees with respect to a long axis of said pharmaceutical reservoir.

23. The system of claim 22, wherein said pharmaceutical reservoir includes a cylindrical bore and said long axis is the longitudinal axis of the bore.

24. The system of claim 11, wherein said skin contact surface includes an adhesive.

\* \* \* \* \*

UNITED STATES PATENT AND TRADEMARK OFFICE
CERTIFICATE OF CORRECTION

PATENT NO. : 10,589,028 B2  
APPLICATION NO. : 15/766472  
DATED : March 17, 2020  
INVENTOR(S) : Oz Cabiri et al.

Page 1 of 1

It is certified that error appears in the above-identified patent and that said Letters Patent is hereby corrected as shown below:

In the Claims

Column 26, Claim number 19, Line number 3, should be corrected as follows:  
The apparatus of claim 17, wherein in said primed position said shield is flush with said frame.

Signed and Sealed this  
Twenty-ninth Day of September, 2020

Andrei Iancu  
*Director of the United States Patent and Trademark Office*